(12) United States Patent
Shadduck

(10) Patent No.: US 7,507,239 B2
(45) Date of Patent: *Mar. 24, 2009

(54) SURGICAL INSTRUMENTS AND TECHNIQUES FOR TREATING GASTRO-ESOPHAGEAL REFLUX DISEASE

(76) Inventor: John H. Shadduck, 1490 Vistazo West St., Tiburon, CA (US) 94920

( * ) Notice: Subject to any disclaimer, the term of this patent is extended or adjusted under 35 U.S.C. 154(b) by 0 days.

This patent is subject to a terminal disclaimer.

(21) Appl. No.: 11/469,816

(22) Filed: Sep. 1, 2006

(65) Prior Publication Data

US 2007/0142831 A1 Jun. 21, 2007

Related U.S. Application Data

(60) Continuation of application No. 11/365,943, filed on Mar. 1, 2006, which is a division of application No. 10/780,027, filed on Feb. 17, 2004, now Pat. No. 7,008,419, which is a division of application No. 09/222,501, filed on Dec. 29, 1998, now Pat. No. 6,740,082.

(60) Provisional application No. 60/086,068, filed on May 20, 1998.

(51) Int. Cl.
*A61B 18/18* (2006.01)
(52) U.S. Cl. ............... 606/41; 606/49; 607/101
(58) Field of Classification Search .............. 606/32, 606/41–50; 607/96–102
See application file for complete search history.

(56) References Cited

U.S. PATENT DOCUMENTS

| | | | |
|---|---|---|---|
| 4,295,464 A | 10/1981 | Shihala | |
| 4,396,019 A | 8/1983 | Perry, Jr. | |
| 4,765,331 A | 8/1988 | Petruzzi et al. | |
| 5,026,366 A | 6/1991 | Leckrone | |
| 5,103,804 A | 4/1992 | Abele et al. | |
| 5,249,585 A | 10/1993 | Turner et al. | |
| 5,341,807 A | 8/1994 | Nardella | |
| 5,395,363 A | 3/1995 | Billings et al. | |
| 5,397,321 A | 3/1995 | Houser et al. | |
| 5,409,458 A | 4/1995 | Khairkhahan et al. | |
| 5,413,557 A | 5/1995 | Solar | |
| 5,425,364 A | 6/1995 | Imran | |
| 5,575,787 A | 11/1996 | Abela et al. | |
| 5,575,788 A | 11/1996 | Baker et al. | |
| 5,651,785 A | 7/1997 | Abela et al. | |
| 5,657,755 A | 8/1997 | Desai | |

(Continued)

OTHER PUBLICATIONS

Wallace et al; U.S. Appl. No. 11/830,251 entitled "Cleaning Devices and Methods," filed Jul. 30, 2007.

(Continued)

*Primary Examiner*—Ahmed M Farah
(74) *Attorney, Agent, or Firm*—Shay Glenn LLP

(57) ABSTRACT

An apparatus to treat tissue in a selected wall region of an esophagus is provided. In one embodiment the apparatus includes an elongate member having a circumference and is sized to be deployed in an esophagus. The apparatus further includes an energy delivery element sized to apply electrical energy to tissue in the esophagus, and to produce a pattern of treated tissue within a less than 180° circumferential portion of the esophagus. The elongate member further includes an expandable structure to stabilize the energy delivery element in physical and electrical contact with tissue.

17 Claims, 15 Drawing Sheets

U.S. PATENT DOCUMENTS

| | | |
|---|---|---|
| 5,681,280 A | 10/1997 | Rusk et al. |
| 5,688,267 A | 11/1997 | Panescu et al. |
| 5,716,340 A | 2/1998 | Schweich, Jr. et al. |
| 5,718,666 A | 2/1998 | Alarcon |
| 5,776,176 A | 7/1998 | Rudie |
| 5,785,705 A | 7/1998 | Baker |
| 5,800,429 A | 9/1998 | Edwards |
| 5,800,486 A | 9/1998 | Thome et al. |
| 5,891,027 A | 4/1999 | Tu et al. |
| 5,897,553 A | 4/1999 | Mulier et al. |
| 5,947,964 A | 9/1999 | Eggers et al. |
| 5,957,920 A | 9/1999 | Baker |
| 6,009,877 A | 1/2000 | Edwards |
| 6,015,407 A | 1/2000 | Rieb et al. |
| 6,033,397 A * | 3/2000 | Laufer et al. ............... 606/27 |
| 6,036,687 A | 3/2000 | Laufer et al. |
| 6,066,139 A | 5/2000 | Ryan et al. |
| 6,066,755 A | 5/2000 | Koch et al. |
| 6,092,528 A * | 7/2000 | Edwards .................. 128/898 |
| 6,401,719 B1 | 6/2002 | Farley et al. |
| 6,645,201 B1 | 11/2003 | Utley et al. |
| 6,689,129 B2 | 2/2004 | Baker |
| 6,740,082 B2 * | 5/2004 | Shadduck .................. 606/41 |
| 6,827,713 B2 | 12/2004 | Bek et al. |
| 7,008,419 B2 * | 3/2006 | Shadduck .................. 606/41 |
| 2006/0149224 A1 * | 7/2006 | Shadduck .................. 606/32 |
| 2008/0097427 A1 | 4/2008 | Stern et al. |

OTHER PUBLICATIONS

Utley et al; U.S. Appl. No. 11/830,291 entitled "Cleaning Device and Methods," filed Jul. 30, 2007.

Kelly et al.; U.S. Appl. No. 12/114,628 entitled "Method and apparatus for gastrointestinal tract ablation for treatment of obesity," filed May 2, 2008.

* cited by examiner

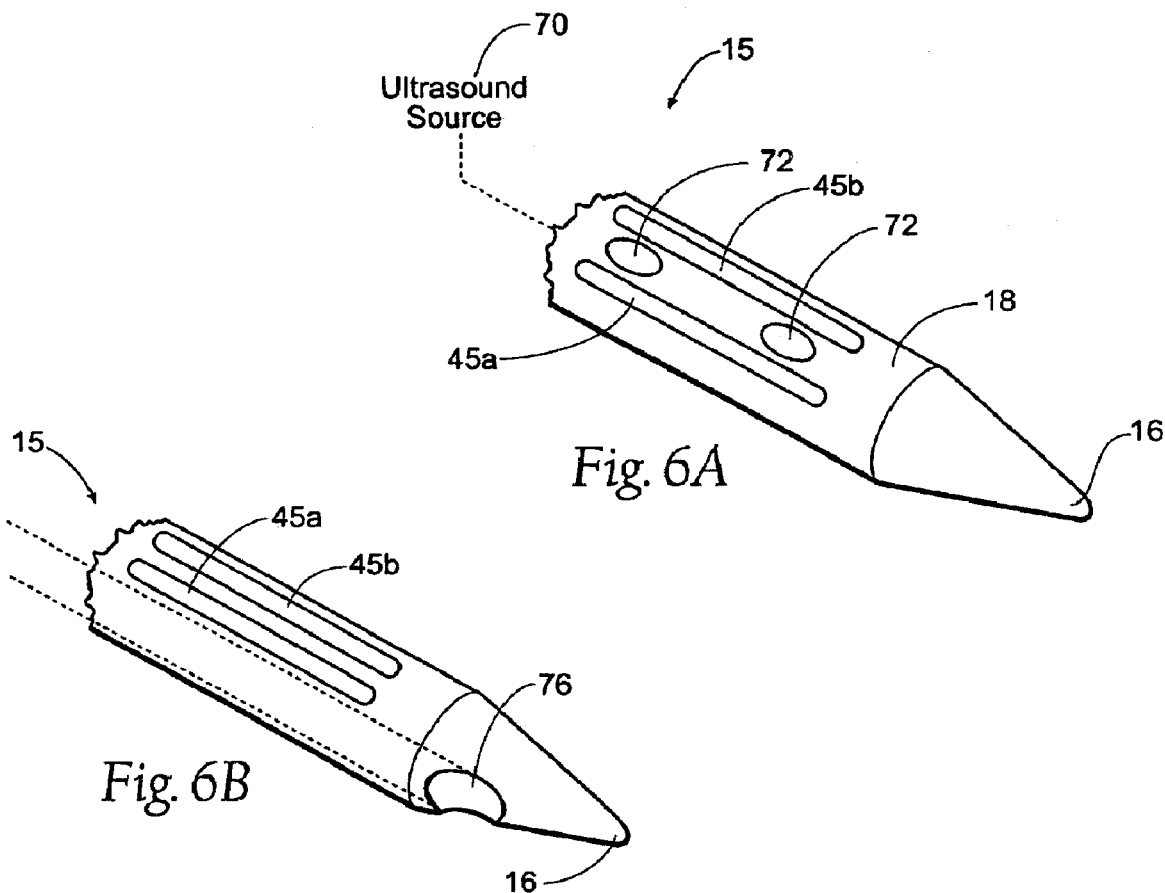
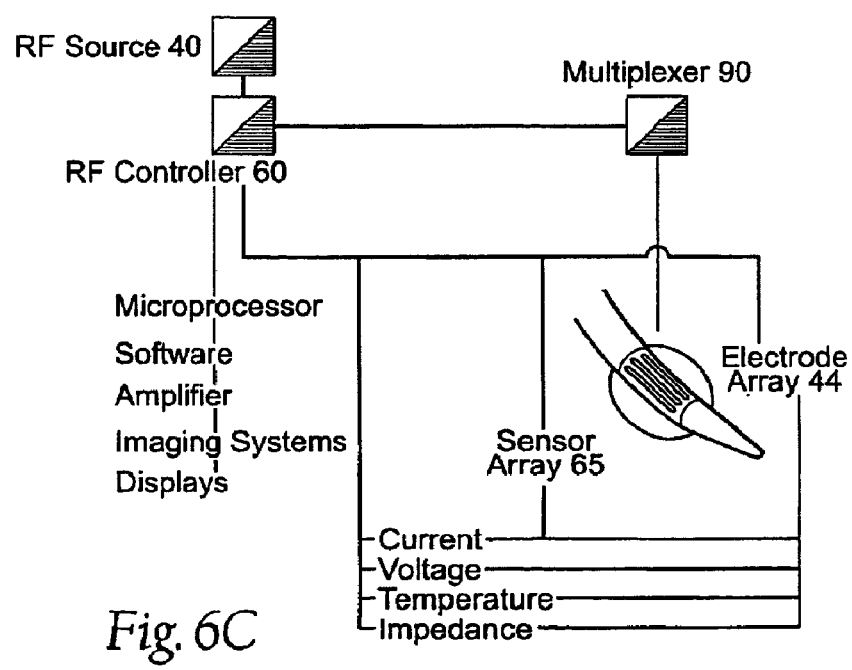

SURGICAL INSTRUMENTS AND TECHNIQUES FOR TREATING GASTRO-ESOPHAGEAL REFLUX DISEASE

CROSS-REFERENCE

This application is a continuation application of Ser. No. 11/365,943, filed Mar. 1, 2006, which is a divisional of U.S. application Ser. No. 10/780,027, filed Feb. 17, 2004 (now U.S. Pat. No. 7,008,419), which is a divisional of U.S. application Ser. No. 09/222,501, filed Dec. 29, 1998 (now U.S. Pat. No. 6,740,082), which claims the benefit of provisional U.S. Application Ser. No. 60/086,068, filed May 20, 1998, and entitled "Surgical Instruments and Techniques for Treating Gastro-Esophageal Reflux Disease," each of which is incorporated herein by reference in its entirety and to which applications we claim priority under 35 USC § 120.

FIELD OF THE INVENTION

This invention relates to instruments and techniques for thermally-mediated therapies of targeted tissue volumes in a patient's LES (lower esophageal sphincter) to treat gastro-esophageal reflux disease (GERD) in a minimally invasive manner. The thermally-mediated treatment, in a low temperature range, selectively injures cells and proteins within the (LES) to induce a predictable wound healing response to populate the targeted tissue with collagen matrices as a means of altering the bio-mechanical characteristics of the LES. In a slightly higher temperature range, an alternative thermally-mediated treatment is used to shrink native collagen fibers within the LES to "model" the dimensions and laxity of the LES. The novel treatment techniques are preferably performed with a trans-esophageally introduced bougie-type instrument and are adapted to take the place of more invasive surgical methods for treating GERD (e.g., Nissen fundoplications) in the treatment of the less severe GERD cases.

BACKGROUND OF THE INVENTION

Gastro-esophageal reflux disease (GERD) is a digestive disorder caused by dysfunction in a patient's lower esophageal sphincter (LES). In normal swallowing, the LES progressively opens to allow food to pass into the stomach and thereafter tightens to prevent food and stomach acids from flowing back into the esophagus. Gastro-esophageal reflux occurs when the stomach's contents flow upwardly into the esophagus. Typically, such acid reflux results from anatomic abnormalities in the LES and surrounding structures, such as overly relaxed muscle tone within the LES, a shortened esophageal length within the abdominal cavity, insufficient intra-abdominal pressures, and/or from a contributory factor such as a hiatal hernia.

Prolonged acid reflux can cause serious complications such as esophagitis, erosions, esophageal bleeding or ulcers. In addition, chronic scarring caused by acid reflux can cause narrowing or stricture in the esophagus. Some patients develop Barrett's esophagus which is a form of severe damage to the esophageal lining. It is believed that Barrett's esophagus is a precursor to esophageal cancer.

As many as 20 million American adults suffer from moderate to severe GERD. For chronic GERD and heartburn, a physician may prescribe medications to reduce acid in the stomach, such as H2-blockers (cimetidine, famotidine, nizatidine and ranitidine). Another form of drug therapy utilizes a proton pump inhibitor (PPI) that inhibits an enzyme in the acid-producing cells of stomach from producing acid (omeprezole, lansoprezole). Yet another form of drug therapy includes motility drugs for quickening the emptying of stomach contents (cisipride, bethanechol and metclopramide). The above-described drug therapies will reduce acid reflux thus reducing pain to the patient, but either have no impact on, or even increase alkaline reflux which can cause severe erosions in the esophagus. Further there exists increasing evidence that lifetime drug therapies can result in atrophic gastritis in certain patients, which is known precursor to Barrett's esophagus.

Since GERD us caused by an anatomic (mechanical) defect, certain surgeries are well suited to correct the defect by effectively lengthening the LES and/or increasing intraluminal pressures within the LES to prevent acid reflux. The leading surgical procedure is an endoscopic Nissen fundoplication, in which the surgeon develops a fold (plication) in the fundus of the stomach and then wraps and sutures the plication generally around the LES to increase intra-esophageal pressures therein. An endoscopic Nissen fundoplication is difficult to perform and typically requires the use of several disposable surgical instruments that are expensive. An open surgery to accomplish a Nissen fundoplication also is possible but undesirable because it requires lengthy postoperative recuperation and results in a long disfiguring upper abdominal incision.

There is therefore a need for a new therapies for treating GERD that offer mechanical or biomechanical solutions to the anatomic defect that underlies gastro-esophageal reflux. Preferably, such new approaches to alleviate acid reflux will not rely on lifetime drug therapies which do not correct the anatomic defect causing acid reflux.

OBJECTS AND SUMMARY OF THE INVENTION

The principal objects of this invention are to provide instruments and techniques for least invasive delivery of thermal energy through a tissue surface to a targeted tissue volume to accomplish the controlled remodeling of the treated tissue, and may also be referred to as bulking tissue. The targeted tissues that can be treated in a "least invasive" manner include, but not limited to, soft tissues in the interior of a body (in particular, collagenous tissues such as fascia, ligamentous tissue), collagen-containing walls of vessels and organs, and anatomic structures having, supporting or containing an anatomic lumen (e.g., esophagus, urethra) Such tissues hereafter may be referred to as "targeted" tissue volumes or "target sites".

More particularly, the invention discloses techniques and instruments that utilize radiofrequency (Rf) energy delivery to selectively injure cells and extracellular compositions (e.g., proteins) in a target site to induce a biological response to the injury—such biological response including cell reproduction to an extent but more importantly the population of the extracellular space with collagen fibers in a repair matrix. Thus, the controlled alteration or modeling of the structural and mechanical characteristics of a targeted tissue site is possible by synthesis of new collagen fibers (or "bulking effects") therein. The above-described objects of the invention are enhanced by controlled manipulation of certain biophysical characteristics of the target tissue prior to the delivery of Rf energy to induce the injury healing process. Besides the synthesis of collagen matrices, another object of the invention is the acute shrinkage of native collagen fibers in the targeted tissue volume. Such acute collagen shrinkage can cause tightening of a targeted tissue volume.

The injury healing process in a human body is complex and involves an initial inflammatory response which in collagenous tissues is followed by a subsequent response resulting in the population of new (nascent) collagen in the extracellular space. A mild injury may produce only an inflammatory reaction. More extensive tissue trauma invokes what is herein termed the injury healing response. Any injury to tissue, no matter whether mechanical, chemical or thermal may induce the injury healing response and cause the release of intracellular compounds into the extracellular compartment of the injury site. This disclosure relates principally to induction of the injury healing process by a thermally-mediated therapy. The temperature required to induce the response ranges from about 40° C. to 70° C. depending on the targeted tissue and the duration of exposure. Such a temperature herein may be referred to as Tncs (temperature that causes "new collagen synthesis"). The temperature needed to cause such injury and collagen synthesis is lower than the temperature Tsc (temperature for acute "shrinkage of collagen") in another modality of the method of the invention disclosed herein.

In order to selectively injure a target tissue volume to induce the population of the extracellular compartment with a collagen matrix, "control" of the injury to a particular tissue is required. In this disclosure, a Rf energy source is provided to selectively induce the injury healing process. (It should be appreciated that other thermal energy devices are possible, for example a laser). In utilizing an Rf energy source, a high frequency alternating current (e.g., from 100,000 Hz to 500,000 Hz) is adapted to flow from one or more electrodes into the target tissue. The alternating current causes ionic agitation and friction in the targeted tissue as the ions follow the changes in direction of the alternating current. Such ionic agitation or frictional heating thus does not result from direct tissue contact with a heated electrode.

In the delivery of energy to a soft tissue volume, I=E/R where I is the intensity of the current in amperes, E is the energy potential measured in volts and R is the tissue resistance measured in ohms. In such a soft tissue volume, "current density" or level of current intensity is an important gauge of energy delivery which relates to the impedance of the tissue volume. The temperature level generated in the targeted tissue volume thus is influenced by several factors, such as (i) Rf current intensity (ii) Rf current frequency, (iii) tissue impedance levels within the targeted tissue volume, (v) heat dissipation from the targeted tissue volume, (vi) duration of Rf delivery, and (vii) distance of the targeted tissue volume from the electrodes. A subject of the present invention is the delivery of "controlled" thermal energy to a targeted tissue volume with a computer controlled system to vary the duration of current intensity and frequency together, based on sensor feedback systems.

In the initial cellular phase of injury healing, granulocytes and macrophages appear and remove dead cells and debris. In the inflammation process, the inflammatory exudate contains fibrinogen which together with enzymes released from blood and tissue cells, cause fibrin to be formed and laid down in the area of the tissue injury. The fibrin serves as a hemostatic barrier and thereafter acts as a scaffold for repair of the injury site. Fibroblasts migrate and either utilize the fibrin as scaffolding or for contact guidance thus further developing a fiber-like scaffold in the injury area. The fibroblasts not only migrate to the injury site but also proliferate During this fibroplastic phase of cellular level repair, a extracellular repair matrix is laid down that is largely comprised of collagen. Depending on the extent of the injury to tissue, it is the fibroblasts that synthesize the collagen within the extracellular compartment as a form of connective tissue (hereafter nascent collagen), typically commencing about 36 to 72 hours after the injury.

Thus, in the injury healing response, compound tissues or organs are repaired by such fibrous connective tissue formation (or matrix formation). Such fibrous connective tissue is the single most prevalent tissue in the body and gives structural rigidity or support to tissues masses or layers. The principal components of such connective tissues are three fiber-like proteins-collagen, reticulin and elastin along with a ground substrate. The bio-mechanical properties of fibrous connective tissue and the repair matrix are related primarily to the fibrous proteins of collagen and elastin. As much as 25% of total body protein is native collagen. In repair matrix tissue, it is believed that nascent collagen is in excess of 50%.

The unique properties of collagen are well known. Collagen is an extracellular protein found in connective tissues throughout the body and thus contributes to the strength of the musculo-skeletal system as well as the structural support of organs. Numerous types of collagen have been identified that seem to be specific to certain tissues, each differing in the sequencing of amino acids in the collagen molecule.

It has been previously recognized that collagen (or collagen fibers as later defined herein) will shrink or contract longitudinally when elevated in temperature to the range of 60° C. to 80° C., herein referred to as Tsc. Portions of this disclosure relate to techniques for controlled shrinkage of collagen fibers in the soft tissue, and more generally to the contraction of a collagen-containing tissue volume, (including both native collagen and nascent collagen) for therapeutic purposes.

Collagen consists of a continuous helical molecule made up of three polypeptide coil chains. Each of the three chains is approximate equal length with the molecule being about 1.4 nanometers in diameter and 300 nm in length along its longitudinal axis in its helical domain (medial portion of the molecule). The spatial arrangement of the three peptide chains in unique to collagen with each chain existing as a right-handed helical coil. The superstructure of the molecule is represented by the three chains being twisted into a left-handed superhelix. The helical structure of each collagen molecule is bonded to together by heat labile intermolecular cross-links (or hydrogen cross-links) between the three peptide chains providing the molecule with unique physical properties, including high tensile strength along with moderate elasticity. Additionally, there exist heat stabile or covalent cross-links between the individual coils. The heat labile cross-links may be broken by mild thermal effects thus causing the helical structure of the molecule to be destroyed with the peptide chains separating into individual randomly coiled structures. Such thermal destruction of the cross-links results in the shrinkage of the collagen molecule along its longitudinal axis to up to one-third of its original dimension, in the absence of tension.

A plurality of collagen molecules (also called fibrils) aggregate naturally to form collagen fibers that collectively make up the a fibrous matrix. The collagen fibrils polymerize into chains in a head-to-tail arrangement generally with each adjacent chain overlapping another by about one-forth the length of the helical domain a quarter stagger fashion to form a collagen fiber. Each collagen fiber reaches a natural maximum diameter, it is believed because the entire fiber is twisted resulting in an increased surface are that succeeding layers of fibrils cannot bond with underlying fibril in a quarter-stagger manner.

Thus, the present invention is directed to techniques and instruments for controlled thermal energy delivery to portions of a patient's LES, in alternative therapies, either:

a) to selectively injury cells and proteins in walls of the LES to induce an injury healing response which populates the extracellular compartment with a collagen fiber matrix ("nascent collagen") to bulk and alter the architecture and flexibility characteristics of tissue volumes within walls of the LES; or b) to, optionally, shrink either "native" collagen or "nascent" collagen in tissue volumes within the wall of the LES to further alter mechanical characteristics of the LES and increase intra-esophageal pressures.

More in particular, the device of the present invention for "modeling" a collagen matrix in targeted tissue (or "bulking" targeted tissue) in walls of the patient's LES is fabricated as a flexible bougie that carries thermal energy delivery means in its distal working end. Typically an Rf source is connected to at least one electrode carried in the working end. The working end may carry a single electrode that is operated in a mono-polar mode or a plurality of electrodes operated in either a mono-polar or bi-polar manner, with optional multiplexing between various paired electrodes. A sensor array of individual sensors also is carried in the working end, typically including (i) thermocouples and control circuitry, and/or (ii) impedance-measuring circuitry coupled to the electrode array.

A computer controller is provided, together with the feedback circuitry from the sensor systems, that is capable of full process monitoring and control of: (i) power delivery; (ii) parameters of a selected therapeutic cycle, (iii) mono-polar or bi-polar energy delivery, and (iv) multiplexing Rf delivery. The controller also can determine when the treatment is completed based on time, temperature, tissue impedance or any combination thereof.

In a first method of the invention, the device is introduced through the patient's mouth until the working end and electrode array is positioned within the LES. The therapeutic phase commences and is accomplished under various monitoring mechanisms, including but not limited to (i) direct visualization, (ii) measurement of tissue impedance of the target tissue masses relative to the device, and (iii) utilization of ultrasound imaging before or during treatment. The physician actuates the pre-programmed therapeutic cycle for a period of time necessary to elevate the target tissue mass to Tncs (temperature of new collagen synthesis) which is from 45° C. to 60° C. depending on duration of energy delivery.

During the therapeutic cycle, the delivery of thermal energy is conducted under full-process feedback control. The delivery of thermal energy induces the injury healing response which thereafter populates the mass with an extracellular collagen matrix and reduces the flexibility of the LES over the subsequent several days and weeks. The physician thereafter may repeat the treatment.

In a second method of the invention, (either the initial or a subsequent therapeutic cycle) the delivery of Rf energy may be elevated to shrink collagen fibers at a range between 60° C. to 80° C. to reach Tsc. The effect of such collagen shrinkage is to rigidify or bulk the treated tissue volumes in the wall of the LES.

Following an initial therapeutic cycle, the treatment can be repeated until the desired increase in intra-esophageal pressures is achieved. It is believed that such periodic treatments (e.g., from 2 to 6 treatments over a period of several weeks) may be best suited to treat the LES.

The above-described modalities of (i) induced synthesis of collagen in collagenous tissues, and (ii) shrinkage of collagen in collagenous tissues describe the effects on LES tissue volumes. These methods of treating the LES are defined herein by a particular temperature range that causes the exact cellular/extracellular effects in the targeted tissue volumes, and are intended to be inclusive of other descriptive terms that may be used to more generally characterize treatments, such as tightening tissue, bulking tissue, fusing or fusion of collagenous tissues, creating scar tissue, sealing or welding collagen-containing tissue, shrinking tissue and the like. The methods disclosed herein are not defined to include ablating tissue, which occurs at higher temperature levels.

In general, the present invention advantageously provides least invasive thermally-mediated techniques for increasing intraluminal pressures in a patient's LES to prevent gastro-esophageal reflux.

The present invention provides novel devices and techniques for thermally inducing an injury healing response to alter cellular/extracellular architecture in the LES.

The present invention provides techniques for thermal induction of bulking of tissue volumes around a sphincter in an anatomic lumen.

The present invention advantageously provides an electrode array fur delivering a controlled amount of Rf energy to a specific targeted tissue volume in the LES having a particular shape or pattern.

The present invention provides an electrode array for delivering a controlled amount of Rf energy to a specific target collagen-containing tissue volume to achieve a controlled contraction of the collagen fibers therein.

The present invention provides a novel device and technique for contraction of collagen fibers around the lumen of an anatomic structure to reduce the dimension of the lumen.

The present invention also provides an instrument and method in which a bougie-type member has a working channel to accommodate an endoscope, an accessory instrument or for therapeutic agent delivery or suction.

The present invention advantageously provides a device that is inexpensive and disposable. Additional advantages and features of the invention appear in the following description in which several embodiments are set forth.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 6A is a view of an alternative embodiment of working end similar to that of FIG. 3A.

FIG. 6B is an alternative embodiment of working end showing a working channel.

FIG. 6C is a block diagram of the Rf source of the invention including a computer controller.

FIG. 7A being a view of positioning the working end in the region of the LES; FIG. 7B being a view of expansion of an optional balloon carried at the working end; FIG. 7C being a view of sectional view of the working end taken along line 7C-7C of FIG. 7B showing the targeted tissue region; and, FIG. 7D showing the tissue dimensions following a thermally mediated therapy.

DESCRIPTION OF THE PREFERRED EMBODIMENT OF THE INVENTION

1. Type "A" Device for Thermally-Mediated LES Therapy.

Figure 1:
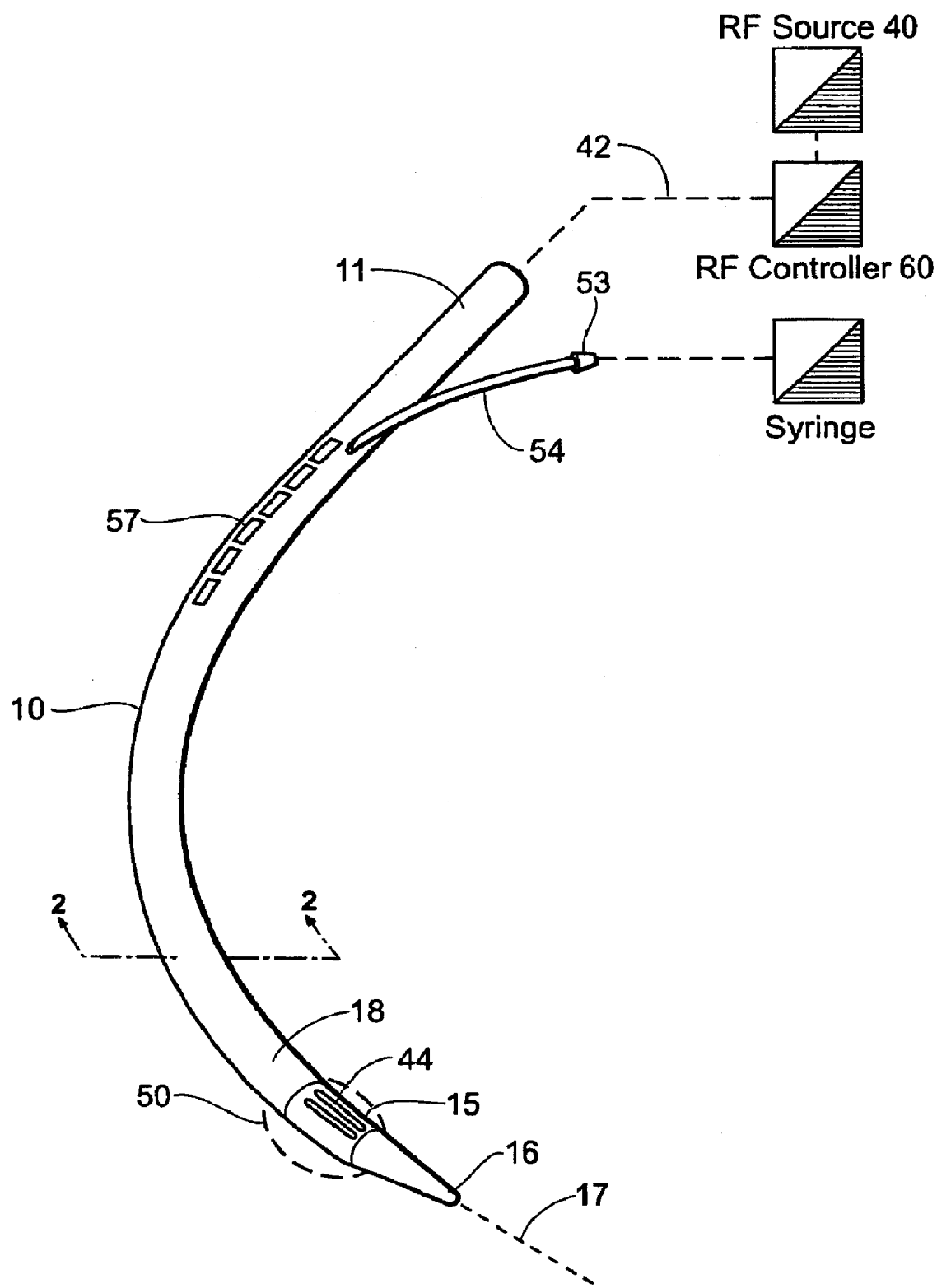
FIG. 1 is a perspective view of a Type "A" device and Rf energy source of the present invention.
Figure 2:
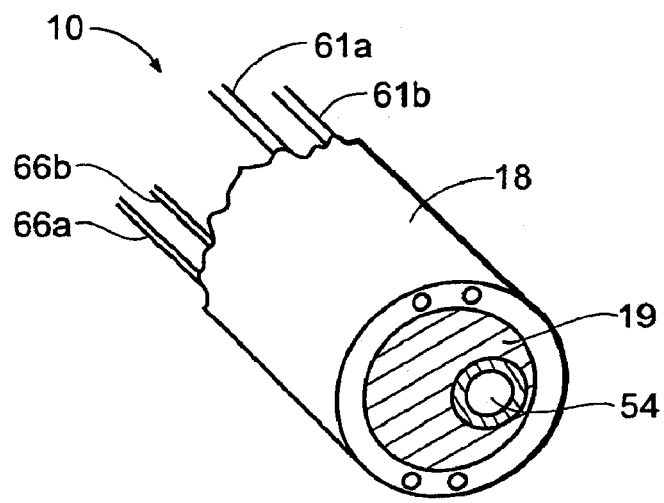
FIG. 2 is transverse sectional view of the device of FIG. 1 taken along line 2-2 of FIG. 1.

By way of example, FIG. 1 depicts LES treatment device 5 that is to be utilized for a thermally-mediated alteration of the cellular/extracellular architecture of a lower esophageal sphincter (LES) while at the same time sizing or gauging the lumen of the esophagus. More in particular, device 5 comprises elongate extension member 10 with proximal end 11 and working end 15 with distal most tip 16. Referring to FIGS. 1 and 2, extension member 10 has a generally cylindrical shape along longitudinal axis 17 with an overall length of approximately 60 to 90 centimeters. The cross-sectional dimension of extension member 10 would typically range in diameters from #40 to #60 French for various patients having varied esophageal anatomies (but may be much smaller as described below for introduction through a working channel of a flexible gastroscope).

The extension member 10 preferably is capable of bending in an approximately 1.0 cm radius (or less) and may comprise a flexible plastic casing 18 with a high-density liquid, gel or other suitable flexible core 19 inside the casing and the tapered tip. The device may compare in size and flexibility to a commercially available bougie that is adapted to push through an esophagus to enlarge the lumen, such as a bougie manufactured by Pilling Week, 420 Delaware Drive, Fort Washington, Pa.

In this Type "A" variant, an Rf energy source 40 is provided for delivering thermal energy to portions of the LES. The Rf energy source 40 may alternatively be replaced with a microwave source, or another known source of thermal energy such as a laser. It further should be appreciated that other sources of energy such as ultrasound or high-energy focused ultrasound (HEFU) that are known in the art may be utilized to cause thermally-mediated treatments of target sites in the LES. The Rf energy source 40 is detachably connected to extension member 10 by power cable 42.

Figure 3A:
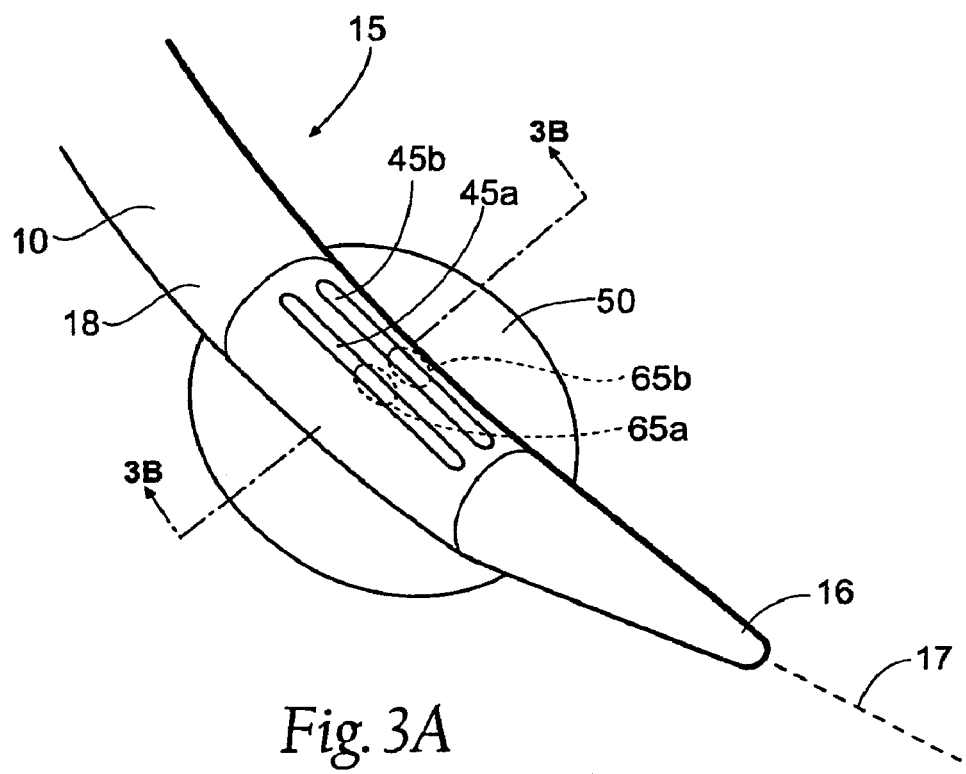
FIG. 3A is an enlarged perspective view of the working end of the device of FIG. 1.

Referring to FIG. 3A, the working end 15 carries at least one electrode in an electrode array 44, and preferably carries a plurality of Rf electrodes 45a-45n that are positioned in the surface 46 of working end 15. FIGS. 1 and 3A show two exemplary electrodes 45a-45b arranged longitudinally in extension member 10 in a spaced relationship in surface 46. The electrodes 45a-45b shown in FIG. 3 may be operated in a mono-polar mode (with ground plate) but preferably are operated in a bi-polar mode to provide controlled energy delivery to achieve a particular temperatures between the adjacent paired electrodes 45a-45b in the wall W of the LES proximate to the electrodes. The electrodes are of any suitable biocompatible conductive material which conduct current to and from tissue around the LES in direct contact with electrodes 45a-45b.

Expansion means are preferably (but optionally) carried in working end 15 for increasing the transverse dimension of the working portion and for pressing any electrodes 45a-45n securely against a wall of the lumen of the LES. Inflatable balloon 50 is capable of collapsed and inflated conditions and is depicted in FIG. 1 (phantom view of inflated condition) and FIGS. 3A and 3B in an inflated condition. Balloon 50 is incorporated into the wall of extension member 10 in this embodiment generally on the opposite side from electrodes 45a-45b. Balloon 50 preferably is made of an elastomeric material, for example silicone or latex and has chamber 52 that is inflatable to a maximum transverse dimension of approximately 10 to 30 millimeters at low pressures (e.g., from 0.5 to 5 psi). A Luer-type fitting 53 is coupled to tube 54 that is provided in core 19 of extension member and communicates with an inflation source to inflate balloon 50, for example a syringe with saline solution or air (FIG. 1). It should be appreciated that the expansion means of the invention is shown as balloon 50 but such expansion means also may comprise any type of suitable mechanical expansion structure disposed within the core of working end 15 that is adapted to expand the cross-section of the working portion that is known in the art (e.g., flexible ribs that are actuated with a pull cable).

Visible and/or radiopaque and markings 57 are shown in FIG. 1 and are used to both angularly and axially position the working end 15 of the device within the patient's LES. The markings 57 in the proximal portion of extension member 10 are useful to the anesthesiologist or physician's assistant to gauge the depth of insertion of the device as well as its rotational angle.

As shown in FIG. 3A, this particular embodiment of device 5 has electrodes 45a-45b each with an elongate shape with the electrodes being longitudinally oriented in relation to axis 17 of extension member 10. Preferably, the electrodes 45a and 45b have a length ranging from about 5.0 mm to 15.0 mm and a width ranging from 0.25 mm to 2.5 mm. The spacing dimension d between the electrodes may range from about 0.5 mm to 10.0 mm.

Figure 3B:
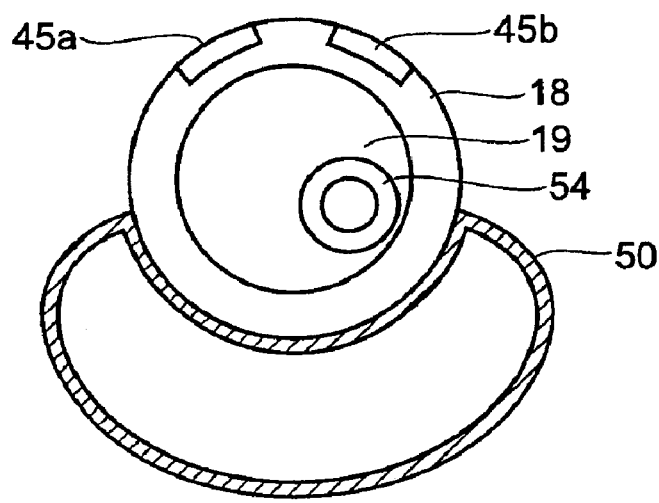
FIG. 3B is transverse sectional view of the working end of FIG. 3A taken along line 3B-3B of FIG. 3A.
Figure 4:
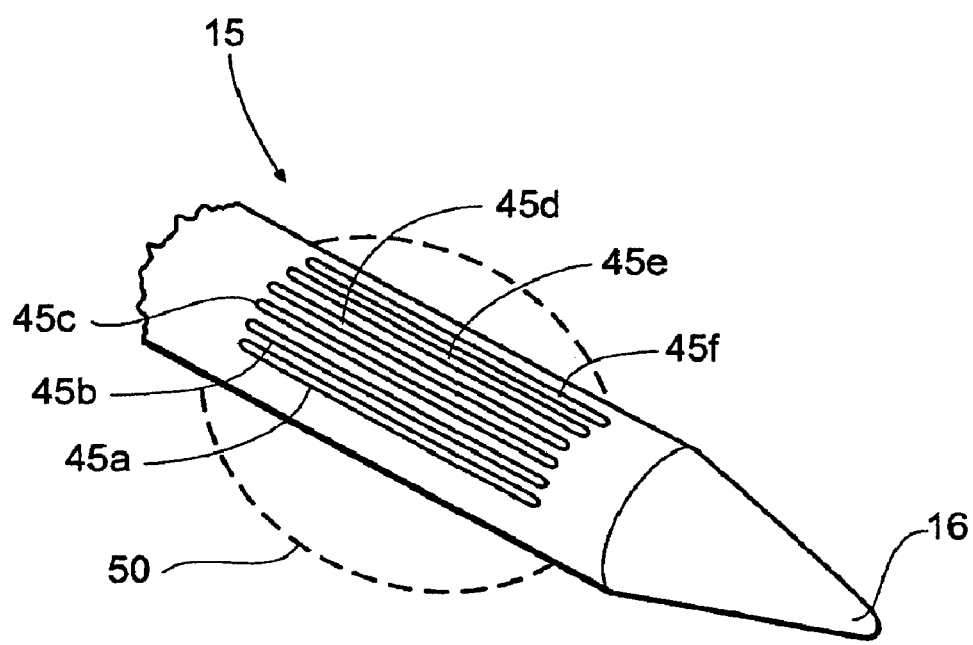
FIG. 4 is a perspective view of an alternative embodiment of working end similar to FIG. 3A.

Although FIGS. 3A-3B show a variant of device 5 with two electrodes 45a and 45b, it should be appreciated that a plurality of greater than two electrodes may be carried in particular spaced relationships along working end 15, as shown in FIG. 4. In FIG. 4, the alternative embodiment is shown with six longitudinal electrodes 45a-45f. The embodiment of FIG. 4 thus may be operated in a mono-polar mode or in a bi-polar mode with a computer controller 60 (see FIG. 1) operatively connected to the Rf source 40 and electrodes and temperature sensors to multiplex (of vector) the current flow between and among various paired electrodes. (It should be appreciated that working end 15 may carry only a single electrode operated in a mono-polar mode and fall within the scope of the invention).

Figure 5A:
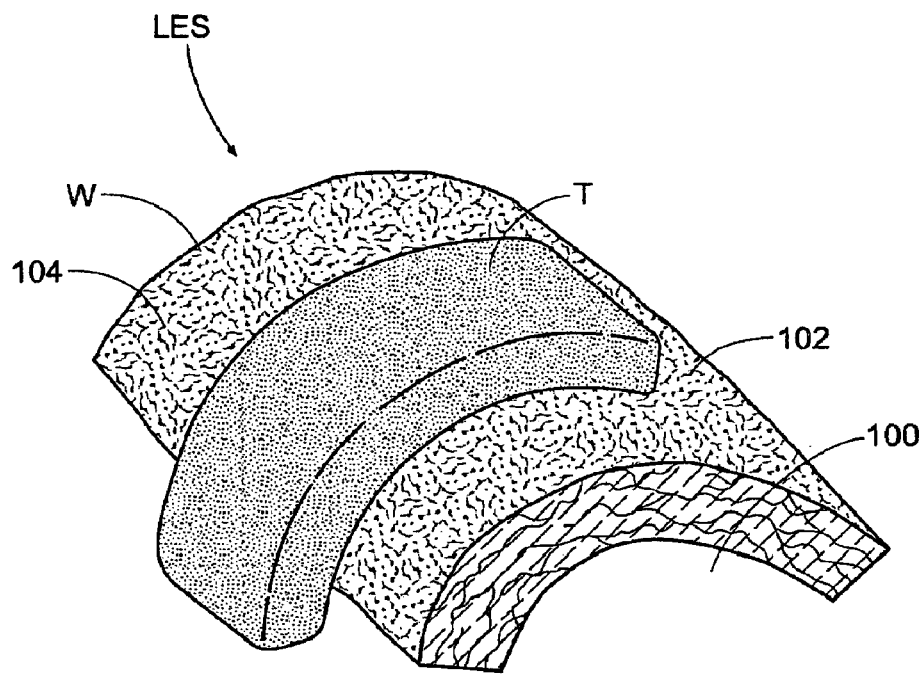
FIGS. 5A-5F are views of a portion of the wall of a lower esophageal sphincter (LES) showing various patterns of thermally-mediated treatments developed by various electrode arrays.
Figure 5B:
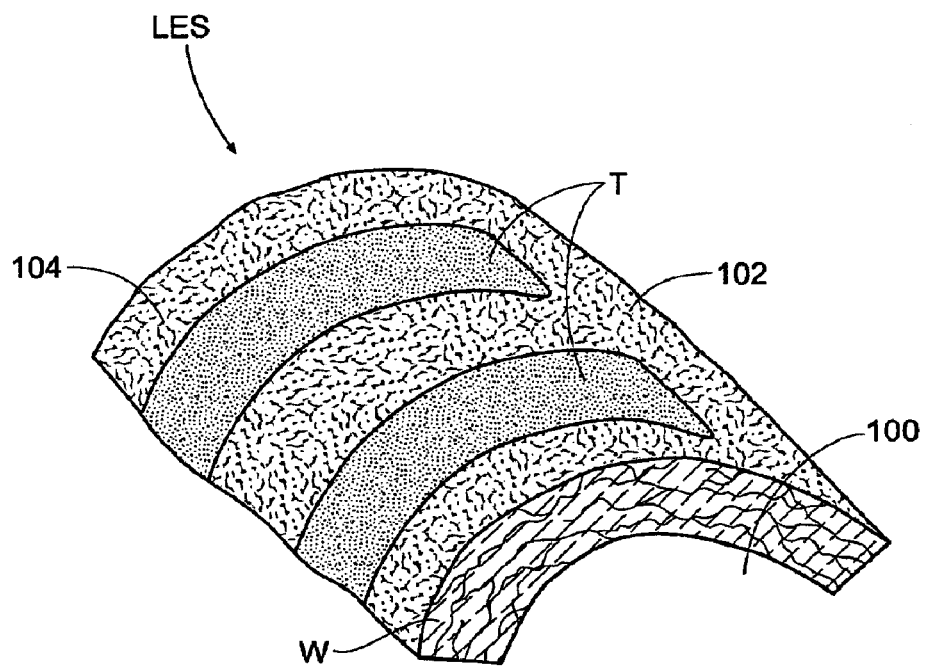
Figure 5C:
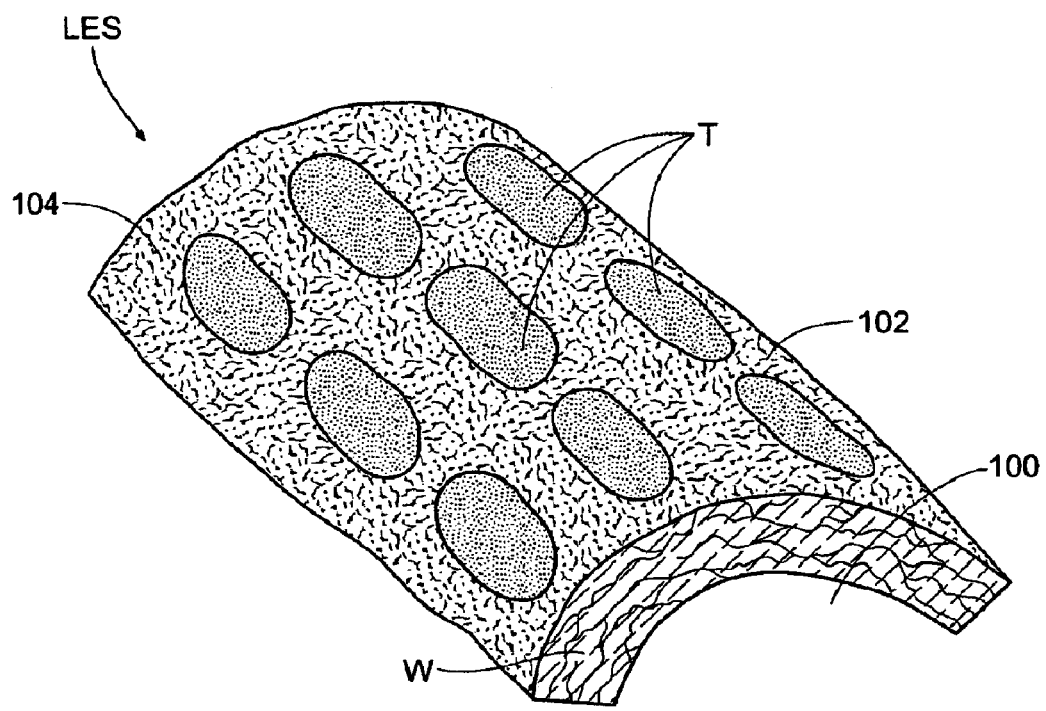
Figure 5D:
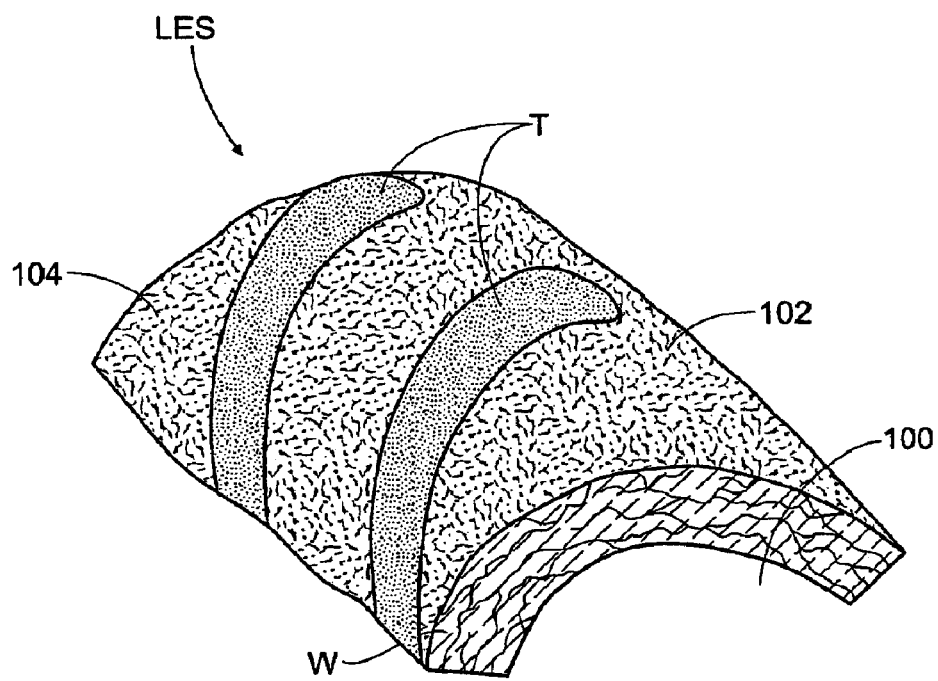
Figure 5E:
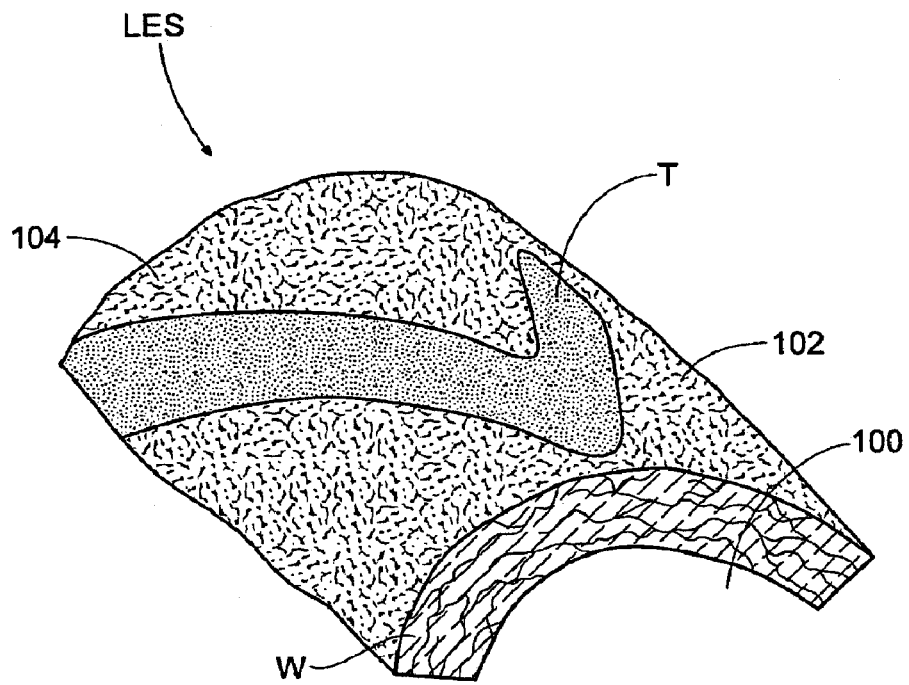
Figure 5F:
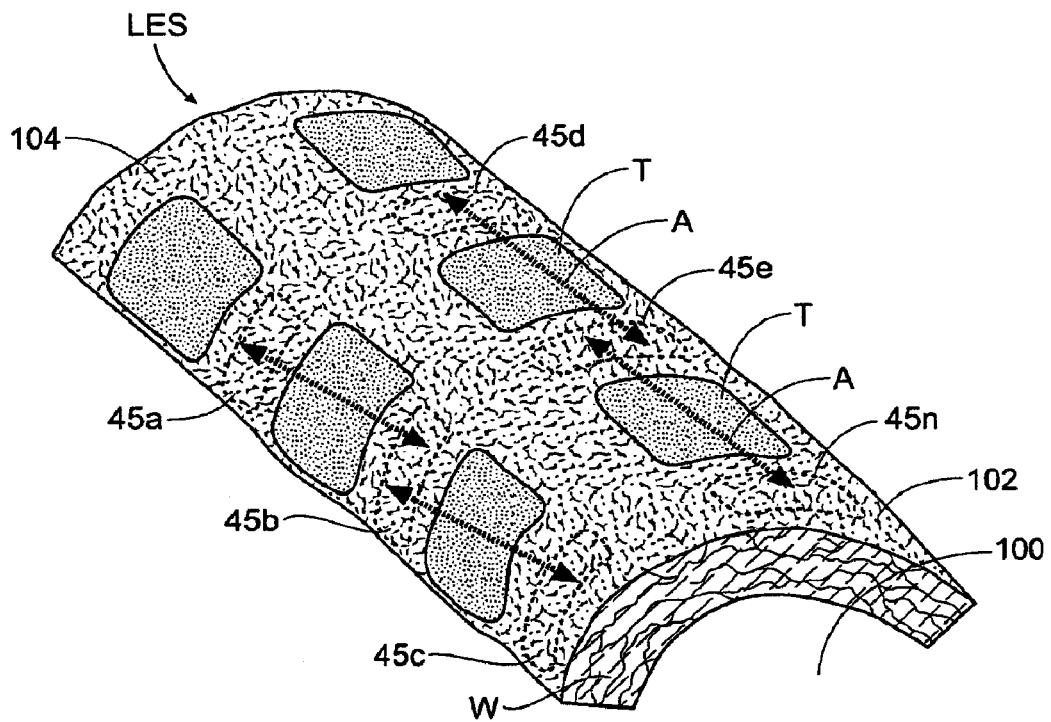

In the preferred embodiment described above, the elongate configuration of the electrodes and their longitudinal orientation was selected because it is believed that Rf energy delivery to elongate regions of the LES will prove optimal to accomplish the objectives of methods of the invention. As will be described below, functional portions of the lower esophageal sphincter extend as much as several cm from the gastroesophageal junction and it is believed that the disclosed thermally-mediated treatments of collagen synthesis should extend over a substantial axial dimension of the LES. Still, another the objective may be collagen shrinkage based on anatomic dimensions and motility studies of a particular patient. Further, the diagnosis may indicate that such collagen shrinkage is desired in a localized annular or part annular region. Thus, other electrode patterns in a "Type A" device are possible and fall within the scope of the invention to deliver particular patterns of thermally-mediated treatment to the wall W of the LES. FIG. 5A shows a singular annular (circumferential) pattern of treated tissue indicated at T in the wall W of a lower esophageal sphincter to shrink collagen and slightly reduce the dimension of the lumen by creating bulk in region T. In FIGS. 5A-5F, treated tissue patterns are shown in portions of wall W (member 10 in phantom view) and it can be understood that electrodes may be of particular configuration to deliver such treatment locations and patterns. (E.g., a single electrode operated in a mono-polar mode (with ground pad) can develop the targeted treatment band T of FIG. 5A, or two parallel electrodes operated in a bi-polar mode may cause the targeted treatment band T of FIG. 5A by energy flow therebetween). FIG. 5B shows multiple annular regions or bands of treated tissue T. FIG. 5C illustrates a multiplicity of treatment regions T as when the objective is the delivery of Rf energy in a diffuse manner over a substantial portion of wall W. FIG. 5D illustrates a plurality of helical treatment regions T which would result in diffuse effects if the regions were close together. FIG. 5E illustrates a v-shaped or chevron-shaped treatment regions T. FIG. 5F is a more greatly enlarged view of wall W with treated regions T multiple electrodes 45a-45n in phantom view. FIG. 5F shown various arrows A that indicate multiplexed vectors of current delivery are possible to cause the thermally-mediated treatments of regions T. Any of the elongate electrodes of FIG. 5A-5E may be configured as multiple intermittently-spaced electrodes and optionally may operate in a bi-polar and multiplexed mode with varied possible vectors between various paired electrodes. Only certain electrodes may delivery current, all for a controlled periods of time. The multiplexer also may cause the Rf energy delivery to switch between mono-polar and bi-polar during a treatment.

In the embodiments shown, the electrodes are of any suitable conductive material which is adapted to deliver Rf energy to soft tissue in the walls W of the LES around the esophageal lumen without ablating (and necrosing) any surface tissue to significant degree. The electrode material may include gold, nickel titanium, platinum, stainless steel, aluminum and copper. Each individual electrode of the array is connected to Rf source 40 and controller 60 by a suitable current-carrying wires 61a-61n within introducer member 10. The proximal portions of such current-carrying wires are carried in power cable 42 that connects with Rf source 40.

Referring back to FIG. 3A it can be seen that a sensor array of individual sensors 65a-65b (an number of sensors are possible) also is provided in a spaced relationship around working end 15. The sensor array will typically include thermocouples or thermisters to measure temperature levels of an electrode or of a portion of the wall W in contact with the sensor. Further, the sensor array includes impedance sensing capabilities (not shown) that measures tissue impedance in a conventional manner between particular electrode elements at the controller 60 as described below. Current-carrying wires 66a-66b are shown in FIGS. 2-3A are connected to sensors 65a-65b. Other wires (not shown) may be provided in the device that could be dedicated specifically to measuring tissue impedance. One or more such impedance monitoring systems may be used to confirm prior to the therapeutic cycle that a satisfactory coupling of energy will be accomplished. Impedance is monitored between each electrode and a ground pad when operated in a mono-polar mode, or between various electrodes when operated in a bi-polar mode.

Another embodiment of a Type "A" device 5 is shown in FIG. 6A wherein an ultrasound source 70 may be coupled to one or more ultrasound transducers 72 (collectively) in a spaced relationship in working end 15 of extension member 10. An output of ultrasound source 70, optionally in combination with Rf source 40, any be adapted to deliver thermal energy to the LES. Each ultrasound transducer 72 may be a piezoelectric crystal mounted on a suitable substrate. A conventional ultrasound lens of electrically insulated material is fitted between the exterior of surface 18 of working end 15 and the piezoelectric crystal which is connected by electrical leads in extension member to ultrasound source 70. Each ultrasound transducer thus is capable of transmitting ultrasound energy into the target tissue of the LES for imaging purposes or high-energy ultrasound (HEFU) to deliver thermal energy. Thermocouples can provide accurate temperature measurements of surface temperatures at various points along the esophageal lumen. Such thermal sensors are preferably adjacent to piezoelectric crystals.

FIG. 6B shows another embodiment of device 5 with a working channel 76, with an open proximal end in the proximal end 11 of the device with a distal termination (not shown) at the distal end of the device. The working channel 76 may be any suitable dimension, for example from about 0.5 mm to 5.0 mm or more, to accommodate a flexible shaft accessory instrument (e.g., an endoscope or forceps). Working channel 76 also may be utilized to deliver therapeutic agents to the patient's stomach or to suction air or liquid secretions from the stomach.

Referring now to FIG. 6C, a block diagram of the Rf source 40 and controller 60 is shown. The controller 60 includes a CPU coupled to the Rf source and multiplexer 80 through a bus. Associated with the controller system may be a keyboard, disk drive or other non-volatile memory system, along with displays that are known in the art for operating such a system. The operator interface may include various types of imaging systems for observing the treatment such as thermal or infrared sensed displays, ultrasonic imaging displays or impedance monitoring displays. The multiplexer 80 is driven by controller 60 (digital computer) which includes appropriate software 82.

In operation, current supplied to individual electrodes 45a-45n along with voltage may be used to calculate impedance. Thermocouples 65 carried in a position proximate to the electrodes together with additional thermal sensors positioned within the Rf source or generator are adapted to measure energy delivery (current and voltage) to each electrode at the site of targeted tissue during a therapeutic cycle. The output measured by thermal sensors is fed to controller 60 in order to control the delivery of power to each electrode location. The controller 60 thus can be programmed to control temperature and Rf power such that a certain particular temperature is never exceeded at a targeted treatment site. The operator further can set the desired temperature which can be maintained. The controller 60 has a timing feature further providing the operator with the capability of maintaining a particular temperature at an electrode site for a particular length of time. A power delivery profile may be incorporated into controller 60 as well as a pre-set for delivering a particular amount of energy. A feedback system or feedback circuitry can be operatively connected to the impedance measuring system, and/or the temperature sensing system or other indicators and to the controller 60 to modulate energy delivery at Rf source 40.

The controller software and circuitry, together with the feedback circuitry, thus is capable of full process monitoring and control of following process variables: (i) power delivery; (ii) parameters of a selected treatment cycle (time, temperature, ramp-up time etc.), (iii) mono-polar or bi-polar energy, and (iv) multiplexing between various electrode combinations. Further, controller 60 can determine when the treatment is completed based on time, temperature or impedance or any combination thereof. The above-listed process variables can be controlled and varied as tissue temperature is measured at multiple sites in contact with the sensor array, as well as by monitoring impedance to current flow at each electrode which indicates the current carrying capability of the tissue during the treatment process. Controller 60 can provide multiplexing along various vectors as previously described, can monitor circuit continuity for each electrode and can determine which electrode is delivering energy.

In FIG. 6C, the amplifier 85 is a conventional analog differential amplifier for use with thermisters and transducers. The output of amplifier 85 is sequentially connected by analog multiplexer 80 to the input of analog digital converter 86. The output of amplifier 85 is a particular voltage that represents the respective sensed temperatures. The digitized amplifier output voltages are supplied to microprocessor 88. Microprocessor 88 thereafter calculates the temperature and/or impedance of the tissue site in question. Microprocessor 88 sequentially receives and stores digital data representing impedance and temperature values. Each digital value received by microprocessor corresponds to a different temperature or impedance at a particular site.

The temperature and impedance values may be displayed on operator interface as numerical values. The temperature and impedance values also are compared by microprocessor with programmed temperature and impedance limits. When the measured temperature value or impedance value at a particular site exceeds a pre-determined limit, a warning or other indication is given on operator interface and delivery of Rf energy to a particular electrode site can be decreased or multiplexed to other electrodes. A control signal from the microprocessor may reduce the power level at the generator or power source, or de-energize the power delivery to any particular electrode site. Controller 60 receives and stored digital values which represent temperatures and impedance sent from the electrode and sensor sites. Calculated skin surface temperatures may be forwarded by controller 60 to display and compared to a predetermined limit to activate a warning indicator on the display.

2. Method of Use of Type "A" Device.

Figure 7A:
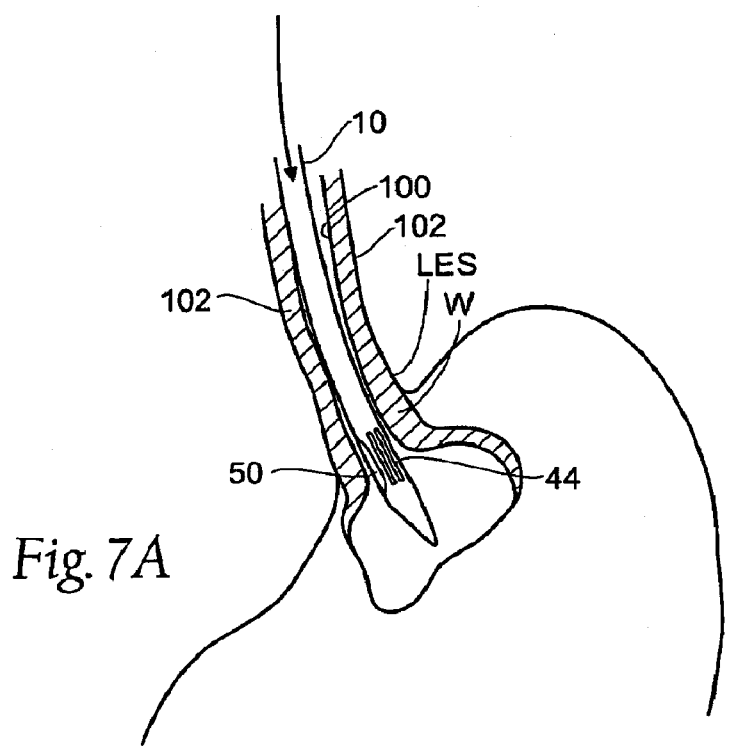
FIGS. 7A-7D are schematic views of a method of thermally-mediated treatment of the LES utilizing the device of FIG. 1.

Operation and use of the instrument shown in FIG. 1 (with two electrode 45a-45b embodiment) in performing the method of the present invention can be described briefly as follows (FIGS. 7A-7D). The physician or an assistant introduces working end 15 of device 5 through the patient's mouth into lumen 100 of esophagus 102. Referring to FIG. 7A, the physician advances extension member 10 distally and rotationally until working end 15 and electrodes 45a and 45b are in a suitable position within the LES (see FIG. 7A). The physician also may advance and turn the instrument to a correct angle by reference to markings 57 on the proximal portion of the device (see FIG. 1). In the illustrations, it is assumed that the targeted tissue is in a quadrant at the patient's left side or at the anterior of the LES (see FIGS. 7A-7B). It is believed the area of treatment will vary from patient to patient as determined by motility studies and anatomic characteristics, and probably most cases will involve treatments in several angular positions within the LES.

Figure 7B:
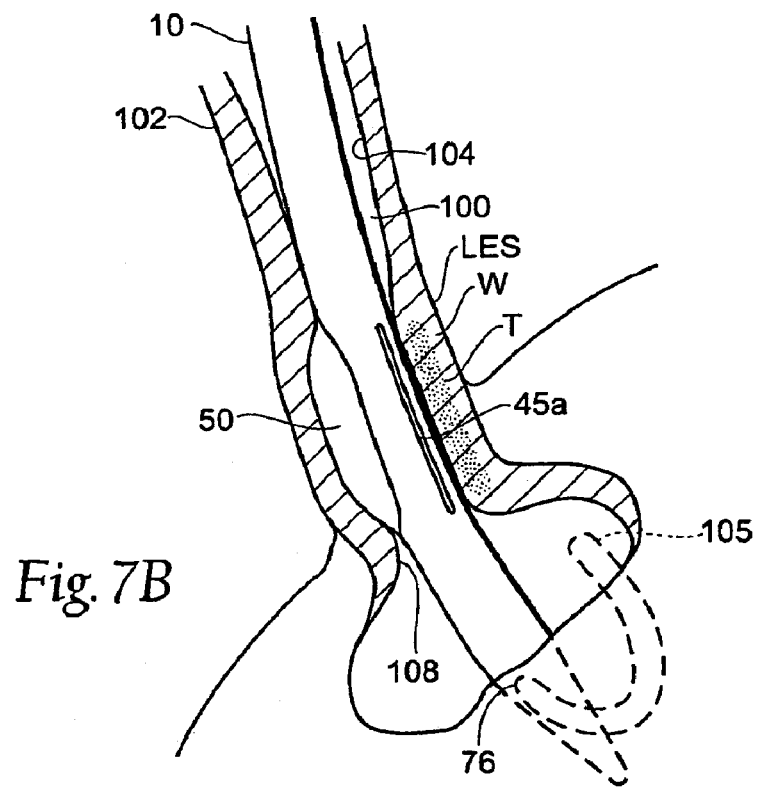
Figure 7C:
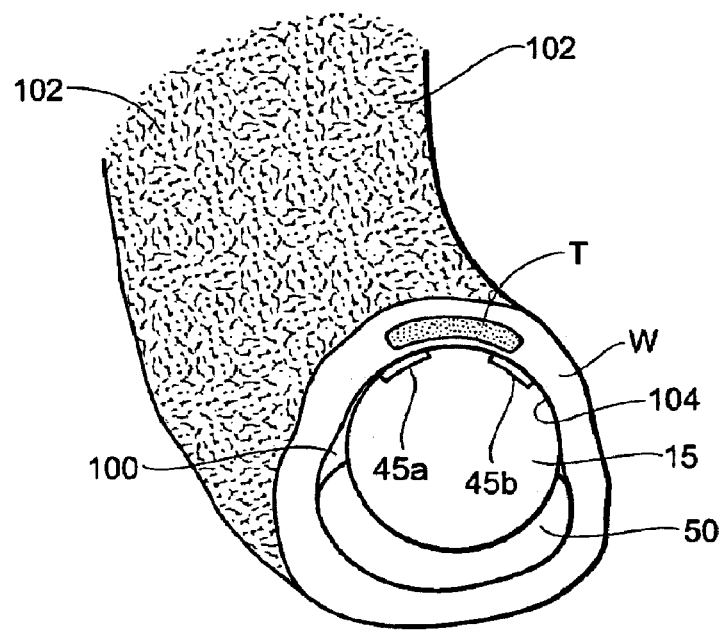

Referring to FIG. 7B, the diameter of extension member 10 may fit somewhat loosely or snugly in esophageal lumen 100 depending on the diameter of device selected. As shown in FIG. 7C, the physician preferably (but optionally) inflates balloon 50 with an inflation medium, for example air or saline solution from a syringe (not shown). Balloon 50 is inflated to a sufficient dimension to press the surface of working end 15, and more particularly electrodes 45a and 45b, into firm contact with surface 104 of targeted tissue in wall W of the LES. (It should be appreciated that a flexible fiberscope 105 (phantom view) may introduced through a optional working channel 76 to view the gastro-esophageal junction 108 from inside the patient's stomach 110 which may be useful in positioning the device (see FIG. 7B)). The physician selects the treatment site based on anatomical knowledge of the LES and is thus capable of avoiding thermal energy delivery to certain areas or sides of the LES if so desired.

Now referring to FIG. 7B, the physician commences the therapeutic phase of Rf delivery under various monitoring mechanisms, including but not limited to, (i) measurement of tissue impedance of the target tissue to determine electrical conductivity between the targeted tissue and the electrode arrangement of device 5, (ii) utilization of ultrasound imaging before and/or during treatment to establish a baseline and duty-cycle tissue characteristics for comparative measurements; and optionally (iii) direct visualization via a fiberscope introduced through a working channel into the stomach and articulated (FIG. 7B). Alternatively, a small diameter flexible scope could be positioned within lumen 100 to view the location of working end 15. (Another similar alternative of delivering the thermally-mediated treatment disclosed herein is to have a small diameter extension member 10 (e.g., 2.0 mm, to 6.0 mm) that can be introduced through the working channel of a flexible scope). All these approaches are similar and can yield the same results in the targeted tissue.

Still referring still to FIG. 7B, the physician may actuate the controller to perform a first modality of treatment described above as a collagen synthesis modality. The controller actuates a preprogrammed therapeutic cycle for a period of time necessary to elevate the targeted tissue T to a particular time/temperature range based on feedback from the sensor system. The cycle can elevate temperatures in the tissue to a range between 40° C. to 70° C. for a period of time ranging from 60 seconds to 10 minutes. More preferably, the therapeutic cycle would elevate temperatures in wall W of the LES to a range between 45° C. and 65° C. for a period of time ranging from 60 seconds to 5 minutes. Still more preferably, the therapeutic cycle would include temperatures in a range between 50° C. and 60° C. for a period of time ranging from 60 seconds to 3 minutes. At the particular selected parameters, the thermal effects will selectively injures cells in and below the surface 104 of wall W at target sites T thus inducing the desired injury healing response. The depth of thermal penetration into the target tissue sites T is determined by the current intensity and duration, and most importantly the thermal relaxation time of the tissue, to preferably effect selective heating of tissue at a depth of about 0.5 mm to 2.5 mm from the surface 104 of the wall W of the lumen 100.

As can be seen in FIG. 7C, electrodes 45*a* and 45*b* are in direct contact with tissue surface 104 of wall W along the tissue-electrode interface. Preferably, the controller 60 will sense temperatures along the tissue-electrode interface by means of the sensor array and/or impedance monitoring system and maintain temperature at the tissue surface 104 at a level below that which ablate the surface, generally by lowering the current intensity or making the energy delivery intermittent. The effect of elevating the temperature of the interior of wall W of the LES without surface ablation can be accomplished because of surface cooling caused by conduction of heat into lumen 100 and the heat-absorbing (heat-sink) characteristics of the working end 15 and extension member 10.

During the therapeutic cycle, the delivery of energy is preferably conducted under full-process feedback control, and in fact the treatment phase may require little attention by the physician ft should be appreciated that the target tissue can be treated uniformly, or various discrete portions of the target tissue can be treated selectively. (In embodiments with a greater number of electrodes, different levels of current can be delivered to different electrode elements, or current can be multiplexed through various electrodes along different vectors as described previously).

A follow-on portion of the therapeutic cycle may comprise a diagnostic phase to gauge the success of the treatment. With energy delivery terminated, diagnosis may be accomplished through (i) direct visualization, (ii) ultrasound imaging, (iv) infrared imaging, or (v) temperature measurements.

Following such a therapeutic cycle to cause collagen synthesis or bulking of target tissue portions around the LES, the patient can return to normal activities with periodic monitoring of the intra-esophageal pressure of the LES as well as muscle response of the LES in conventional motility studies. Thereafter, the same treatment may be repeated until alterations in cellular/extracellular architecture increases intraluminal pressures within the LES to the desired level. It is believed that periodic treatments (e.g., 1 week to 2 weeks between treatments) is best suited to alter the mechanical characteristics of the LES. The thermally-mediated treatment induces a bodily response which includes populating the targeted tissue sites T with nascent collagen in the extracellular spaces, which after periodic treatments will make walls W of the LES to be bulked up or thicker and which will cause a reduced cross-section of lumen 100 within the LES.

If the physician elects to tighten the LES to a greater extent, he may in an initial treatment or in subsequent treatment, perform a different modality of thermally-mediated treatment described above as the collagen shrinkage modality. In this case, the physician elects to deliver elevated levels of Rf energy to contract or shrink collagen fibers to further tighten or reduce the flexibility of target tissue T within wall portions of the LES. The delivery of Rf energy will shrink collagen fibers as described above in the LES without significant modification of adjacent tissue volumes. The temperature gradients described above can be accomplished to achieve the temperature to contract collagen fibers in the targeted tissue without increasing the temperature of the surface 104 so that the surface tissue will not be ablated, blistered or necrosed. The energy level is monitored and controlled as to each individual electrode as detailed above by controller 60. The energy delivery is continuously changed based on sensor inputs which includes temperature data and impedance data from the sensors provided in the device.

Figure 7D:
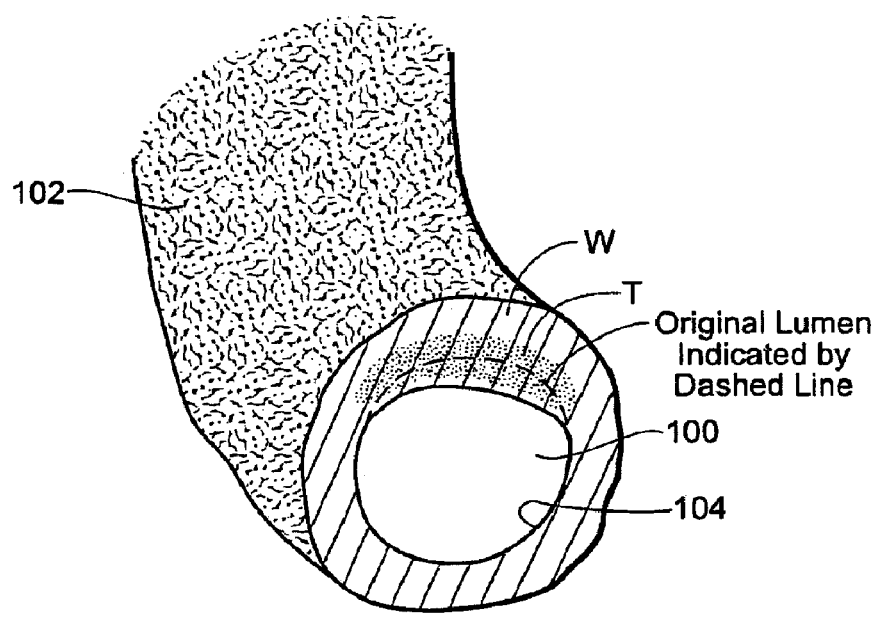

In the collagen shrinkage modality of treatment, a preprogrammed therapeutic cycle is selected to achieve shrinkage of native collagen. In this case, the delivery of energy is controlled to elevate temperatures in target tissue T to a range generally between 60° C. to 80° C. Preferably, the therapeutic cycle can be controlled to attain temperatures in the targeted tissue in a range from 60° C. and 70° C. for a period of time ranging from 60 seconds to 5 minutes. Immediate acute longitudinal shrinkage of collagen fibers and molecules will occur in such a temperature range. Thus, the targeted tissue T shrink generally in the direction of collagen fibers therein and will make the walls around the lumen of the esophagus somewhat tighter and resistant to radial extension (opening). Looking at the thermally-mediated effects on such collagenous tissue from a different perspective, the collagen fibers and molecules are increased greatly in caliber, as described above, thus causing a bulking up of the targeted tissue in the LES (see FIG. 7D). In other words, the native collagen (and collagen matrices) will bulk up and tighten the targeted tissue sites T as shown in FIG. 7D. If the therapy is performed following a prior collagen synthesis treatment at the lower temperature ranges described above, the follow collagen shrinkage therapy can be enhanced since both the nascent and native collagenous tissue will shrink within the target tissue sites T. Each subsequent treatment not only will populate the tissue sites T with additional nascent collagen fibers, but also shrinks the nascent collagen fibers from the prior treatment or treatments.

3. Type "B" Device for Thermally-Mediated LES Therapy.

Figure 8A:
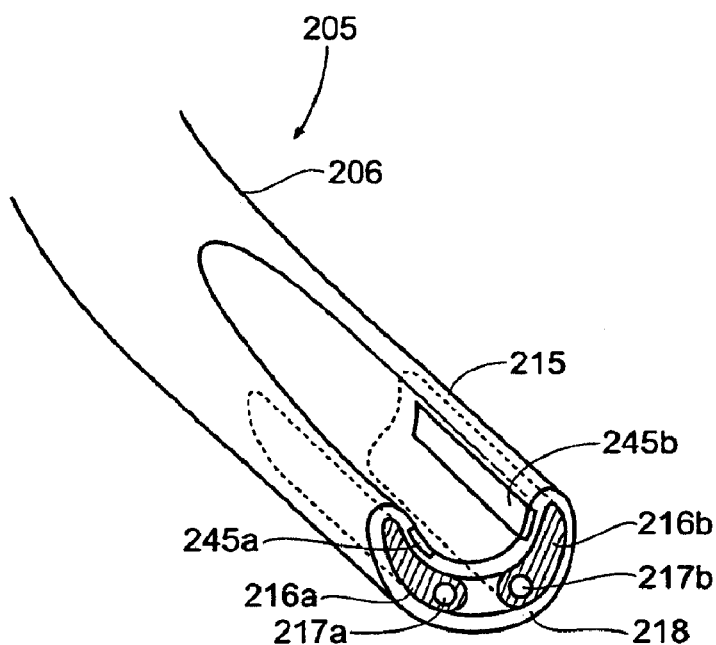
FIGS. 8A-8B are views of the working end of a Type "B" of device for thermally-mediated therapies of the LES and its means of capturing the wall of the LES for treatment.
Figure 8B:
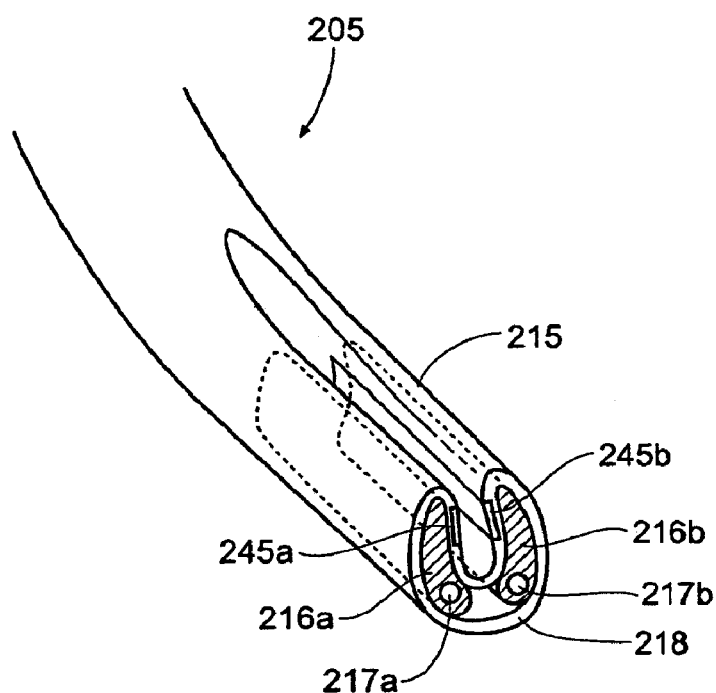
Figure 9:
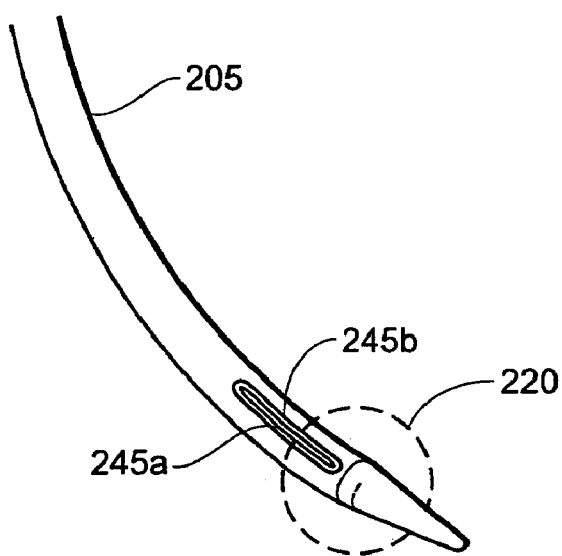
FIG. 9 is a view of the working end of an alternative Type "B" devices similar to the device FIGS. 8A-8B.

By way of example, FIGS. 8A-8B and 9 depict an alternative type of LES treatment device that may be utilized for Rf energy delivery to wall portions W of the LES to alter its cellular/extracellular architecture. More in particular, the system includes an embodiment of elongate device or member 205 with a medial extending portion 206 that is substantially similar to the Type "A" device described above, and elements common to both the Type "A" and Type "B" embodiment will be described with the same reference numerals. As shown in FIG. 8A-8B, the working end 215 of this embodiment carries a tissue-engaging means known in the art comprising an openable/closeable arm structure for engaging target tissue in the wall of the LES (Cf. the openable/closeable arm structure of related Provisional Application Ser. No. 60/024,974 filed on Aug. 30, 1996; and follow-on patent application Ser. No. 09/920,291 filed on Aug. 28, 1997, which disclosures are incorporated herein in their entirety by this reference). FIG. 8A shows a longitudinally-oriented arm structure with arm elements 216*a* and 216*b* that are rotatable around pivots 217*a* and 217*b* and are optionally covered within a thin flexible sheath 218 that carries longitudinal electrodes 245*a* and 245*b*. FIG. 8B shows that arm elements 216*a* and 216*b* are articulatable from a proximal handle of the device by cables and articulating means known in the art thereby to capture tissue of wall W therebetween. It should be appreciated that the electrodes may be carried directly on the arm elements without a covering sheath. The sheath, however, is preferred to make the instrument perform similar to a bougie for ease of introduction into a patient's esophagus.

Referring to FIG. 9, the elongate device 205 further may include an inflatable collar 220 that can be inflated with any suitable medium, for example air or saline solution from a syringe (not shown). Collar 220 is shown in phantom view in an inflated condition and is position around a distal portion of the device. Collar 220 is sufficiently large to prevent it from passing through GE-junction as the device is lifted proximally and thus may serve as a means of positioning electrodes 245a and 245b and the articulating arm elements in the LES.

Figure 10:
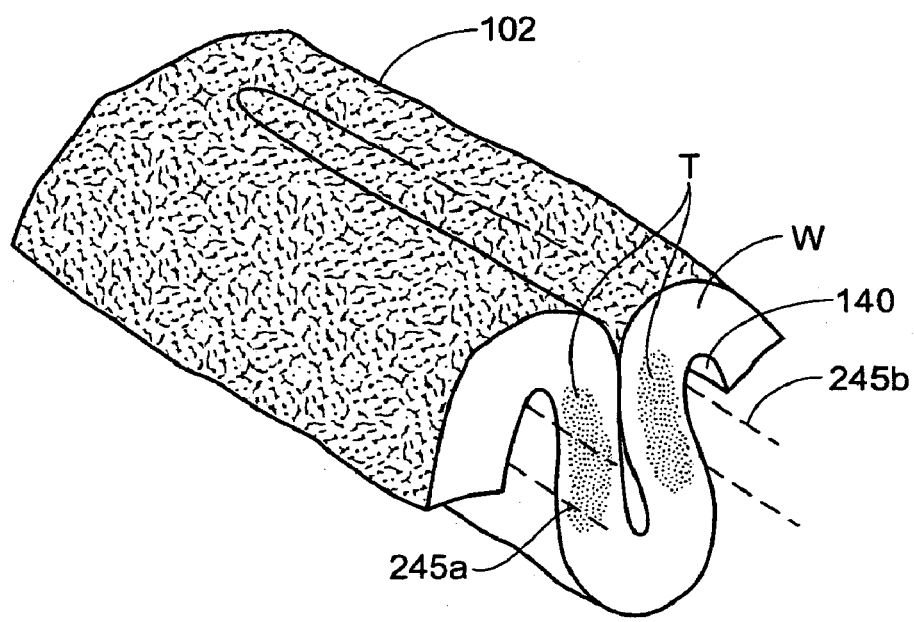
FIG. 10 is a view of a portion of the wall of the LES showing a method of treatment with a Type "B" device.

In operation, a portion of the wall of the LES is shown in sectional view in FIG. 10 being captured and engaged by arm elements 216a and 216b (phantom view) of working end 215. The sectional view depicts the targeted tissue T as a hatched regions in interiors of the wall W of the LES as when Rf energy is delivered in a bi-polar manner between the paired electrodes (mono-polar flow also is possible). The treatment may be in a single location or repeated in a plurality of locations. In order for the arm elements and sheath 218 to better engage the well of the LES, gripping elements known in the art may be configured in the sheath or arm elements to grip tissue (e.g., penetrating elements; tissue gripping studs, or suction apertures communicating with remote suction source) and are intended be encompassed by the scope of the invention.

Figure 11A:
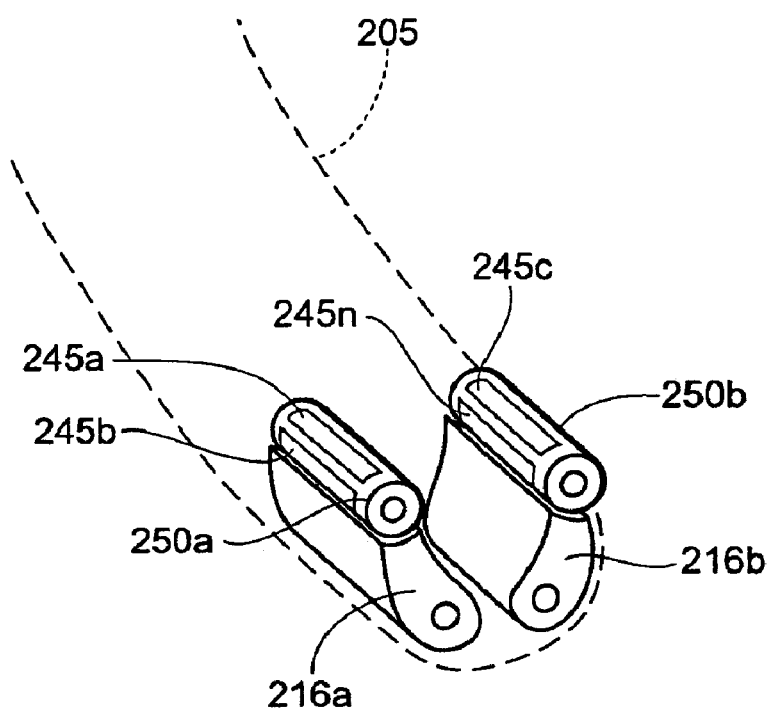
FIG. 11A is a view of the working end of another alternative Type "B" with rolling components.
Figure 11B:
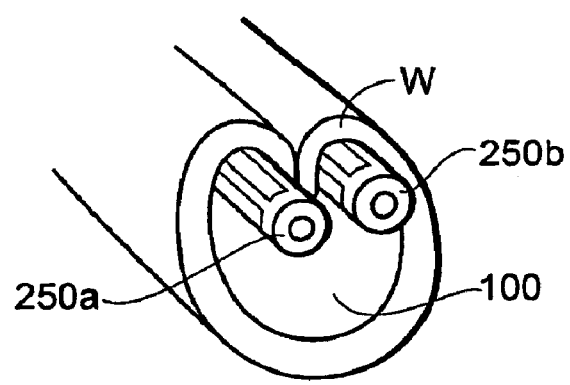
FIG. 11B is a view of a portion of the wall of the LES showing a method of treatment with the working end of FIG. 11A.

FIG. 11A illustrates another embodiment of Type "B" device in which roller elements 250a and 250b are carried in arm elements 216a and 216b to progressively the engage the wall W of the LES and delivery Rf energy between various paired electrodes 245a-245n in the roller elements 250a and 250b. This manner of Rf energy delivery was disclosed in Provisional Application Ser. No. 60/024,974 filed on Aug. 30, 1996 and follow-on patent application Ser. No. 09/920,291 filed on Aug. 28, 1997, and incorporated therein Provisional Application Ser. No. 60/022,790 filed on Jul. 30, 1996 titled Less Invasive Surgical Instruments and Techniques for Treating Sleep Apnea and Snoring; all of which applications are incorporated herein in their entirety by this reference. (In the earlier disclosures, one of the applications of Rf energy delivery was to model the flexibility of a patient's soft palate by means of collagen synthesis and/or collagen shrinkage therein). FIG. 11B is a sectional view of a small portion of the LES with a wall W engaged between rollers 250a and 250b and targeted tissue T receiving Rf energy as described above.

Figure 12A:
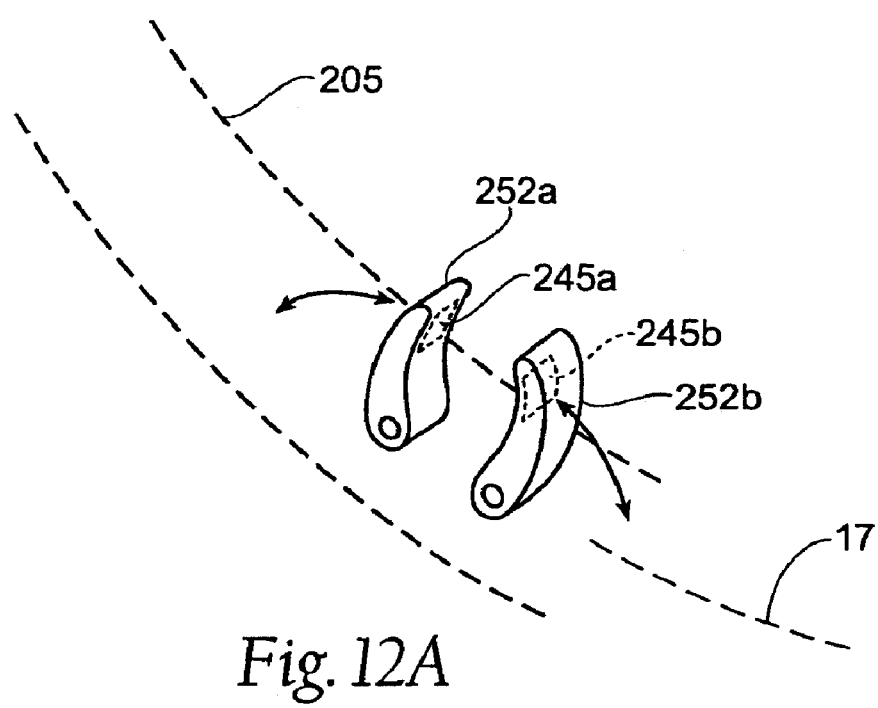
FIG. 12A is a view of the working end of yet another Type "B" device.
Figure 12B:
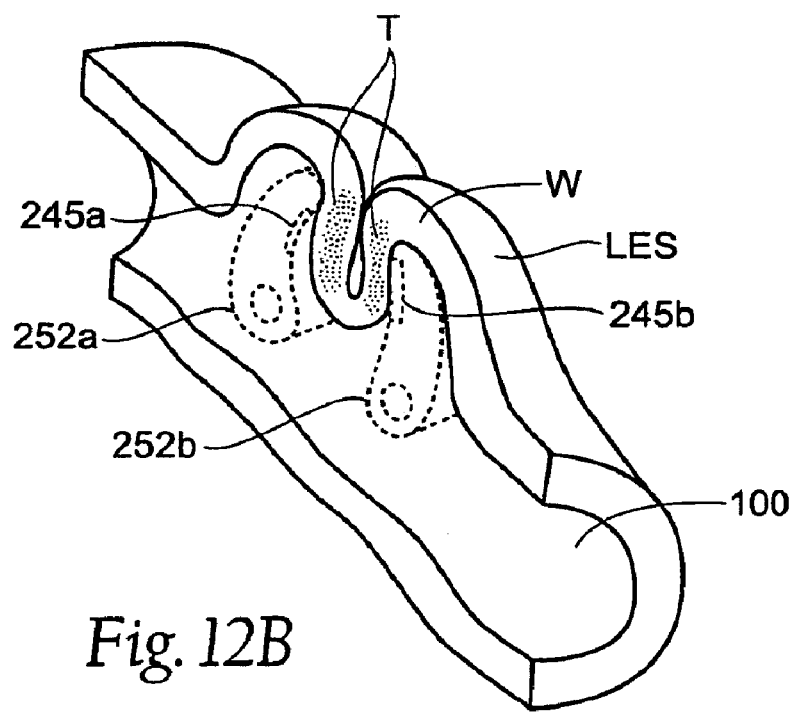
FIG. 12B is a view of a portion of the wall of the LES showing a method of treatment with the working end of FIG. 12A.

Another variant of Type "B" device is shown in FIG. 12A in which articulating arm elements 252a and 252b are carried in a manner to engage the wall W of the LES at 90.degree. to the previously described embodiment. In other words, the articulating elements 252a and 252b are adapted to capture a portion of wall W treat tissue in a fold around a part of a circumference of the LES rather than in a longitudinal fold described previously. Such a manner of capturing tissue and delivering Rf energy to the wall W of an organ was disclosed in Provisional Application Ser. No. 60/024,974 filed on Aug. 30, 1996 and follow-on patent application Ser. No. 09/920, 291 filed on Aug. 28, 1997 (incorporated herein by reference). FIG. 12B is a view of a small portion of the LES with a wall W engaged by articulating elements 252a and 252b and further indicating targeted tissue T receiving Rf energy in any of the manners described previously.

4. Type "C" System for Thermally-Mediated LES Therapy.

Figure 13A:
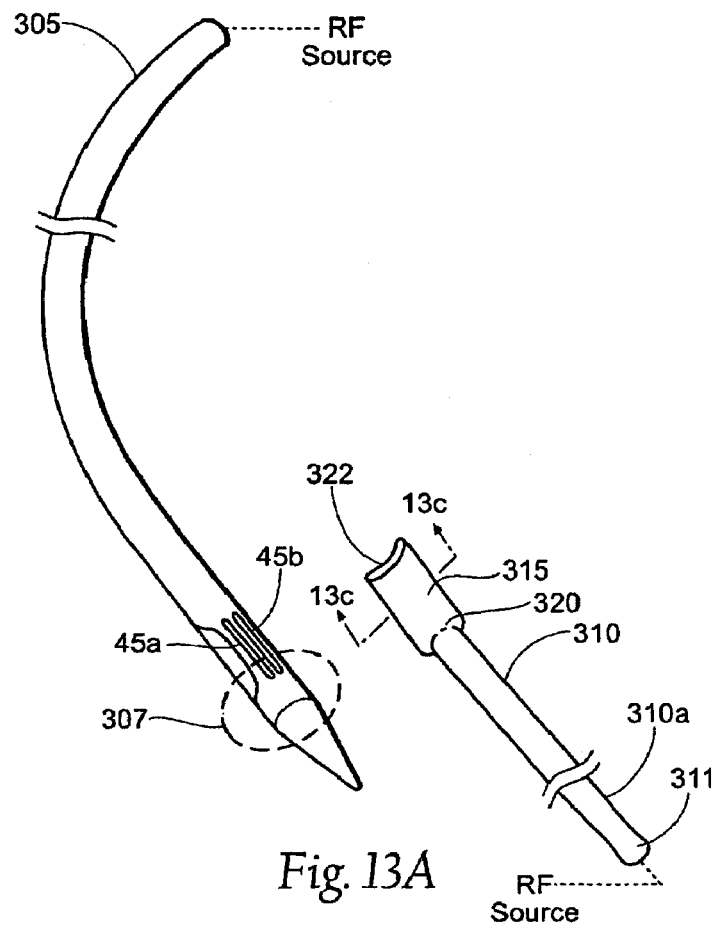
FIG. 13A is a view of a Type "C" device system for thermally-mediated treatments of the LES.
Figure 13B:
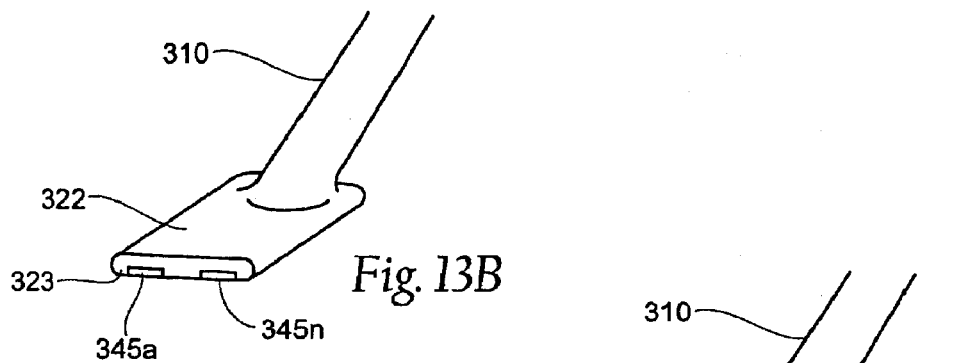
FIG. 13B is a view of the working end of a component of the Type "C" system of FIG. 13A.
Figure 13C:
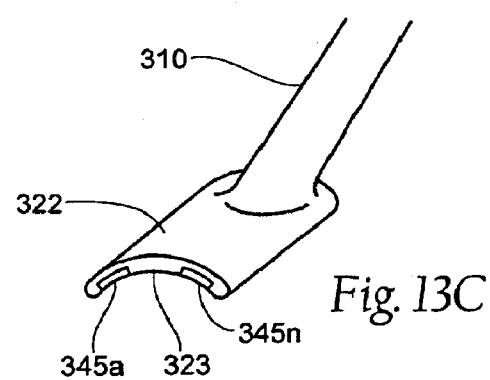
FIG. 13C is a views of an alternative working end similar to that of FIG. 13B.

By way of example, FIGS. 13A-13C depict an alternative of LES treatment system that may be utilized for performing the above-described methods of treating a lower esophageal sphincter, but this time with the assistance of a separate device from the exterior of the LES in an endoscopic procedure. At the same time, an intraluminal device is used to size or gauge lumen 100 of the esophagus 102. More in particular, the system includes intraluminal esophageal device 305 which is substantially similar to the Type "A" device described above, and hereafter will have similar elements described with the same reference numerals as used above in the Type "A" device. The intraluminal device 305 further includes an inflatable collar 307 that can be inflated with any suitable medium, for example air or saline solution from a syringe (not shown). Collar 307 is shown in phantom view in an inflated condition and is position around a distal portion of the device. Collar 307 is sufficiently large to prevent it from passing through the GE-junction as the device is lifted proximally as a means of positioning electrodes 45a-45n in the LES.

Intraluminal device 305 cooperates with extraluminal device 310 also shown in FIG. 13A-13C. The extraluminal device 310 has elongate introducer member with proximal end 310a and is adapted for introduction in the interior of the body through a cannula (e.g., a 5-20 mm trocar sleeve) working end 315 is carried in the distal portion of introducer member 310a and comprises an articulatable of flexible section 320 section that has a esophagus-contacting surface portion 322. The esophagus-contacting portion 322 may be substantially planar (see FIG. 13B) but preferably has an at least partial circumferential receiving surface 323 for fitting closely around the esophagus 102 when intraluminal device 305 is positioned within lumen 100 of the esophagus (see FIG. 13C).

Figure 14:
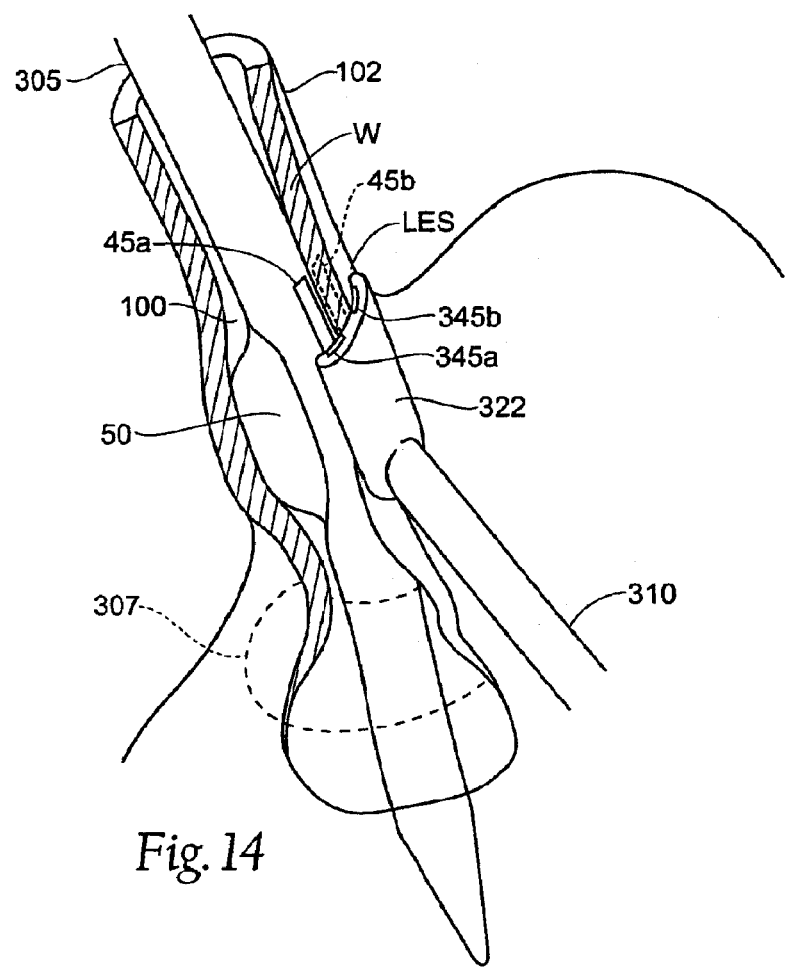
FIG. 14 is a view of the wall of the LES showing a method of treatment with the Type "C" system of FIG. 13A.

As can be seen in FIGS. 13A, the extraluminal device 310 has at least one and preferable a plurality of electrodes 345a-345n within working end 315. FIG. 14 shows in a (sectional) perspective view that the electrodes 345a-345n of extraluminal device 310 are adapted to cooperate with electrodes 45a-45b of intraluminal device 305. In use, the electrodes of the two devices, 305 and 310, preferably are adapted to operate in a bi-polar manner with current passing from the extraluminal device to the intraluminal device or vice versa, or in a bi-polar manner between paired electrodes in the extraluminal member with the intraluminal electrodes not activated but facilitating current flow through wall W (or vice versa). Further, the bi-polar operation of the device may be along a various multiplexed vectors as described previously. The extraluminal device may have all the temperature sensing capabilities, impedance monitoring capabilities, and other feedback capabilities of the Type "A" device described above.

Alternatively, another embodiment of extraluminal device may be used to deliver a thermally-mediated treatment as described above, but only from the exterior of the esophagus to targeted tissue in the LES. In some cases, Rf energy delivery only from the exterior of the LES may be preferred because it would then be unnecessary to elevate the temperature of surface 104 or mucous membrane of the esophageal lumen 100. As described above, the exterior approach logically would be performed only when the surgeon needed to endoscopically access the patient's abdominal cavity for other reasons, e.g., to treat a hiatal hernia that sometimes contributes to GERD. Since several ports are necessary to endoscopically correct a hiatal hernia, the use of such an extraluminal instrument would make such a procedure no more invasive. In either a mono-polar or bi-polar operating mode, the intraluminal device may simply be a conventional bougie to "stent" the esophagus while performing the thermally-mediated Rf treatment of the LES from its exterior with device 310. FIG. 14 shows the positioning of the devices 305 and 310 in a manner of practicing a method of the invention The extraluminal device may have an articulatable working end so that the esophagus-contacting portion may be easily oriented to lay against the LES. Such a working end may be hinged or flexible by any suitable means (e.g., a pull wire or reciprocating rod mechanism), with the specific articulation characteristics partly dependent on the location of the port which is used to introduce the device into the patient's body.

Figure 15:
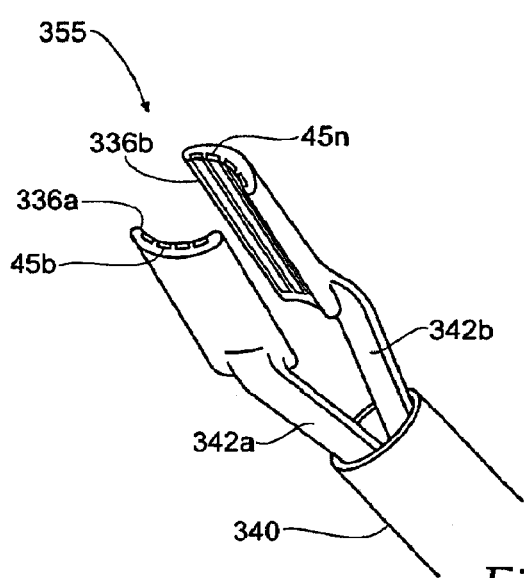
FIG. 15 is a view of the working end of another Type "C" device

FIG. 15 depicts another embodiment of LES treatment device 335 that may be utilized for thermally-mediated treatment of the LES from its exterior in an endoscopic procedure. This embodiment of extraluminal device has any suitable closing mechanism for closing the at least two esophagus-contacting portions 336a and 336b around the LES and esophagus. Such an embodiment would allow the delivery of thermal energy at least partly around the circumference of the LES, and even entirely around the circumference of the LES if so desired. This embodiment would require that the distal esophagus and LES be mobilized before utilizing the device. Again, this device would find use in cases that require repair of a hiatal hernia wherein mobilization of the distal esophagus is required. As shown in FIG. 15, the two esophagus-contacting portions 336a and 336b are actuated by reciprocation of sleeve 340 over cam-type elements 342a and 342b.

It should be appreciated that the combination of intraluminal and extraluminal devices are preferably indexable by any suitable means, by which is meant that it would be desirable to have electrodes of the intraluminal device and the electrodes of the cooperating extraluminal device maintainable in a particular alignment or registration, both axially and angularly. A preferable means is to provide a fiber optic light source in the intraluminal component of the system that will transilluminate the wall W of the LES, thereby allowing the physician to position markings (or apertures) on the extraluminal device relative to the points of transillumination. The two esophagus-contacting portions of the extraluminal instrument are preferably made of a transparent plastic material.

It should be appreciated that the surface 18 of working end 15 may carry cooling means as known in the art, wherein cooling lumens may circulate a coolant fluid within the extension member to maintain the surface 104 of the esophageal lumen 100 at a cooled temperature. Alternatively, the extension member may carry the semiconductor Peltier cooling means disclosed in co-pending U.S. patent application Ser. No. 09/110,065 filed Jul. 3, 1998 titled Semiconductor Contact Lens Cooling System and Technique for Light-Mediated Eye Therapies. It should also be appreciated that variations on the thermally-mediated treatments disclosed herein may be accomplished with penetrating needle-type electrodes in a working end 15 as known in the art that can be actuated from a handle portion of an elongate member although this is not a preferred approach.

From the foregoing it can be seen that there are provided techniques and instruments that will selectively accomplish thermally-mediated treatments of targeted collagenous tissues in a patient's LES without substantially necrosing or ablating the surface 104 of the esophageal lumen 100. The device can be utilized to selectively injure cells to induce a biological response to populate target tissue site T with a collagen fiber matrix. The device further can be utilized to contract collagen-containing tissue volumes to reduce the diameter of the lumen of LES. It can be readily understood that such techniques of tissue modeling may be applied to other lumens of other anatomic structures in the body. For example, a treatment for urinary incontinence can be effected to shrink tissue, tighten tissue or rigidify tissue with a collagen matrix around the urethra with a trans-urethral Rf instrument. Similarly, tissues around a patient's soft palates can be treated. Specific features of the invention are shown in some figures and not in others, and this is for convenience only and any feature may be combined with another in accordance with the invention. While the principles of the invention have been made clear in the exemplary Type "A" through Type "C" versions, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. An apparatus to treat tissue at a targeted site in an esophagus comprising:
    an extension member sized with a central axis for deployment in an esophagus;
    an expansion structure on the extension member, and
    a radio frequency energy delivery element on the extension member positioned at a radial position closer to the central axis of the extension member than the expandable structure.

2. The apparatus of claim 1, further comprising a radiofrequency energy source connected to the energy delivery element.

3. The apparatus of claim 2, wherein the radiofrequency energy is at a frequency of at least 100 kHz.

4. The apparatus of claim 3, wherein the radiofrequency energy is delivered at a frequency between 100 kHz and 500 kHz.

5. The apparatus of claim 2, wherein the radiofrequency energy is bipolar.

6. The apparatus of claim 1, wherein the energy delivery element is an array of a plurality of electrodes.

7. The apparatus of claim 1, wherein the expansion structure is an inflatable balloon.

8. The apparatus of claim 7 wherein the balloon is inflatable to a maximum transverse dimension of approximately 10 to 30 millimeters at pressures of about 0.5 psi to about 5 psi.

9. The apparatus of claim 1, wherein the expansion structure is a mechanical structure.

10. The apparatus of claim 1, wherein the energy delivery element is configured to deliver energy to the targeted site in an annular or part annular pattern.

11. The apparatus of claim 1, wherein the energy delivery element is configured to deliver energy to the targeted site in a pattern of multiple annular or multiple part annular regions.

12. The apparatus of claim 1 wherein the expansion structure is radially opposite the energy deliver element on the extension member.

13. The apparatus of claim 1 wherein the expansion structure occupies a circumferential arc of less than 180 degrees on the exterior surface of the extension member.

14. The apparatus of claim 1 wherein the energy delivery element occupies a circumferential arc of about 90 degrees on the exterior surface of the extension member.

15. The apparatus of claim 1, wherein the energy delivery element is a single electrode operated in a mono-polar mode.

16. The apparatus of claim 1, wherein the energy delivery element includes electrode pairs which are operated in a multiplexing mode.

17. The apparatus of claim 1, wherein the energy delivery element is configured to deliver energy to the targeted site in a pattern of multiple regions.

* * * * *